US007279327B2

(12) United States Patent
Curtis et al.

(10) Patent No.: US 7,279,327 B2
(45) Date of Patent: Oct. 9, 2007

(54) METHODS FOR PRODUCING RECOMBINANT CORONAVIRUS

(75) Inventors: Kristopher M. Curtis, Chapel Hill, NC (US); Boyd Yount, Hillsborough, NC (US); Ralph S. Baric, Haw River, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 33 days.

(21) Appl. No.: 10/474,962

(22) PCT Filed: Apr. 19, 2002

(86) PCT No.: PCT/US02/12453

§ 371 (c)(1),
(2), (4) Date: May 25, 2004

(87) PCT Pub. No.: WO02/086068

PCT Pub. Date: Oct. 31, 2002

(65) Prior Publication Data

US 2004/0235132 A1      Nov. 25, 2004

Related U.S. Application Data

(60) Provisional application No. 60/285,320, filed on Apr. 20, 2001, provisional application No. 60/285,318, filed on Apr. 20, 2001.

(51) Int. Cl.
*C12N 15/85* (2006.01)
*C12N 15/63* (2006.01)
(52) U.S. Cl. .................. 435/325; 435/320.1; 424/221.1
(58) Field of Classification Search ............. 435/320.1, 435/325
See application file for complete search history.

(56) References Cited

OTHER PUBLICATIONS

Godeke et al. J. Virol. 2000, vol. 74, pp. 1566-1571.*
Izeta et al. J. Virol. Feb. 1999, vol. 73, No. 2, pp. 1535-1545.*
Fisher et al. J. Virol. 1997, vol. 71, No. 7, pp. 5148-5160.*
Goldeke, G.A., *Assembly of Spike into Coronavirus Particles is Mediated by the Carboxy-Terminal Domain of the Spike Protein*, J. Virol., Feb. 2000, vol. 74, No. 3:1566-1517.
Yount, B., *Strategy for Systematic Assembly of Large RNA and DNA Genomes: Transmissible Gastroentritis Virus Model*, J. Virol., Nov. 2000, vol. 74, No. 22:10600-10611.
Curtis, K.M., *Heterologous Gene Expression from Transmissible Gastroenteritis Virus Replicon Particles*, J.Virol., Feb. 2002, vol. 76, No. 3:1422-1434.
Ortego, J., *Generation of a Replication-Competent, Propagation-Defecient Virus Vector based on the Transmissible Gastroenteritis Coronavirus Genome*, J. Virol., Nov. 2002, vol. 76, No. 22: 11518-11529.
International Search Report, PCT/US02/12453, Mar. 13, 2003.
Baudoux et al. "Coronavirus Pseudoparticles Formed with Recombinant M and E Proteins Induce Alpha Interferon Synthesis by Leukocytes" *Journal of Virology* 72(11):8636-8643 (1998).
Bos et al. "The Production of Recombinant Infectious DI-Particles of a Murine Coronavirus in the Absence of Helper Virus" *Virology* 218:52-60 (1996).
de Haan et al. "Coronavirus Particle Assembly: Primary Structure Requirements of the Membrane Protein" *Journal of Virology* 72(8):6838-6850 (1998).
Fuerst et al. "Eukaryotic transient-expression system based on recombinant vaccinia virus that synthesizes bacteriophage T7 RNA polymerase" *Proc. Natl. Acad. Sci. USA* 83:8122-8126 (1986).
Vennema et al. "Intracellular Transport of Recombinant Coronavirus Spike Proteins: Implications for Virus Assembly" *Journal of Virology* 64(1):339-346 (1990).
Vennema et al. "Nucleocapsid-independent assembly of coronavirus-like particles by co-expression of viral envelope protein genes" *The EMBO Journal* 15(8):2020-2028 (1996).
Pushko et al. "Replicon-Helper Systems from Attenuated Venezuelan Equine Encephalitis Virus: Expression of Heterologous Genes in Vitro and Immunization against Heterologous Pathogens in Vivo" *Virology* 239:389-401 (1997).
Schutz-Cherry et al. "Influenza (A/HK/156/97) Hemagglutinin Expressed by an Alphavirus Replicon System Protects Chickens against Lethal Infection with Hong Kong-Origin H5N1 Viruses" *Virology* 279:55-59 (2000).
Hevey et al. "Marburg Virus Vaccines Based upon Alphavirus Replicons Protect Guinea Pigs and Nonhuman Primates" 251:28-37 (1998).
Percy et al. "A Poliovirus Replicon Containing the Chloramphenicol Acetyltransferase Gene Can Be Used To Study the Replication and Encapsidation of Poliovirus RNA" *Journal of Virology* 66(8):5040-5046 (1992).

(Continued)

*Primary Examiner*—Bruce R. Campell
*Assistant Examiner*—Bao Quh Li
(74) *Attorney, Agent, or Firm*—Myers, Bigel, Sibley & Sajovec, P.A.

(57) ABSTRACT

A helper cell for producing an infectious, replication defective, *coronavirus* (or more generally nidovirus) particle cell comprises (a) a nidovirus permissive cell; (b) a nidovirus replicon RNA comprising the nidovirus packaging signal and a heterologous RNA sequence, wherein the replicon RNA further lacks a sequence encoding at least one nidovirus structural protein; and (c) at least one separate helper RNA encoding the at least one structural protein absent from the replicon RNA, the helper RNA(s) lacking the nidovirus packaging signal. The combined expression of the replicon RNA and the helper RNA in the nidovirus permissive cell produces an assembled nidovirus particle which comprises the heterologous RNA sequence, is able to infect a cell, and is unable to complete viral replication in the absence of the helper RNA due to the absence of the structural protein coding sequence in the packaged replicon. Compositions for use in making such helper cells, along with viral particles produced from such cells, compositions of such viral particles, and methods of making and using such viral particles, are also disclosed.

14 Claims, 11 Drawing Sheets

OTHER PUBLICATIONS

Messerte et al. "Cloning and mutagenesis of a herpesvirus genome as an infectious bacterial artificial chromosome" *Proc. Natl. Acad. Sci. USA* 94:14759-14763 (1997).

Khromykh et al. "Subgenomic Replicons of the Flavivirus Kunjin: Construction and Applications" *Journal of Virology* 71(2):1497-1505 (1997).

Fischer et al. "Analysis of Constructed E Gene Mutants of Mouse Hepatitis Virus Confirms a Pivotal Role for E Protein in Coronavirus Assembly" *Journal of Virology* 72(10);7885-7894 (1998).

Fischer et al. "Analysis of a Recombinant Mouse Hepatitis Virus Expressing a Foreign Gene Reveals a Novel Aspect of Coronavirus Transcription" *Journal of Virology* 71(7):5148-5160 (1997).

Dubensky et al. "Sindbis Virus DNA-Based Expression Vectors: Utility for In Vitro and In Vivo Gene Transfer" *Journal of Virology* 70(1):508-519 (1996).

DiCiommo et al. "Rapid, High Level Protein Production Using DNA-based Semliki Forest Virus Vectors" *The Journal of Biological Chemistry* 273(29):18060-18066 (1998).

Caley et al. "Humoral, Mucosal, and Cellular Immunity in Response to a Human Immunodeficiency Virus Type 1 Immunogen Expressed by a Venezuelan Equine Encephalitis Virus Vaccine Vector" *Journal of Virology* 71(4):3031-3038 (1997).

Bredenbeek et al. "Sindbis Virus Expression Vectors: Packaging of RNA Replicons by Using Defective Helper RNAs" *Journal of Virology* 67(11):6439-6446 (1993).

Almazan et al. "Engineering the largest RNA virus genome as an infectious bacterial artificial chromosome" *PNAS* 97(10):5516-5521 (2000).

Agapov et al. "Noncytopathic Sindbis virus RNA vectors for heterlogous gene expression" *Proc. Natl. Acad. Sci. USA* 98:12989-12994 (1998).

Meulenberg et al. "Infectious Transcripts from Cloned Genome-Length cDNA of Porcine Reproductive and Respiratory Syndrome Virus" *Journal of Virology* 72(1):380-387 (1998).

Curtis et al. "Reverse Genetic Analysis of the Transcription Regulatory Sequence of the Coronavirus Transmissible Gastroenteritis Virus" *Journal of Virology* 78(11):6061-6066 (2004).

Yount et al. "Reverse genetics with a full-length infectious cDNA of severe acute respirator syndrome coronavirus" *PNAS* 100(22):12995-13000 (2003).

Vamavski et al. "Stable High-Level Expression of Heterologous Genes In Vitro and in Vivo by Noncytopathic DNA-Based Kunjin Virus Replicon Vectors" *Journal of Virology* 74(9):4394-4403 (2000).

Porter et al. "Encapsidation of Genetically Engineered Poliovirus Minireplicons Which Express Human Immunodeficiency Virus Type 1 Gag and Pol Proteins upon Infection" *Journal of Virology* 67(7):3712-3719 (1993).

Balasuriya et al. "Expression of the Two Major Envelope Proteins of Equine Arteritis Virus as a Heterodimer Is Necessary for Induction of Neutralizing Antibodies in Mice Immunized with Recombinant Venezuelan Equine Encephalitis Virus Replicon Particles" *Journal of Virology* 74(22):10623-10630 (2000).

Berglund et al. "Enhancing immune responses using suicidal DNA vaccines" *Nature Biotechnology* 16:562-565 (1998).

Liljestrom et al. "A New Generation of Animal Cell Expression Vectors Based On The Semliki Forest Virus Replicon" *Biotechnology* 9:1356-1361 (1991).

Dollenmaier et al. "Membrane-Associated Respiratory Syncytial Virus F Protein Expressed from a Human Rhinovirus Type 14 Vector Is Immunogenic" *Virology* 281:216-230 (2001).

Mendez et al. "Molecular Characterization of Transmissible Gastroenteritis Coronavirus Defective Interfering Genomes: Packaging and Heterogeneity" *Virology* 217:495-507 (1996).

Curtis et al. "A Simple Strategy to Assemble Infectious RNA and DNA Clones" *Adv. Exp. Med. Biol.* 494:475-481 (2001).

Curtis et al. "Coronavirus Dervied Vectors for Genetic Analysis and Heterologous Gene Expression" *Recent Res. Devel. Virol.* 4:203-229 (2002).

Khromykh et al. "Replicon-based vectors of positive strand RNA viruses" *Current Opinion in Molecular Therapeutics* 2(5):555-569 (2000).

Yount et al. "Biological consequences of TGEV Gene Rearrangement" 20th Annual American Society for Virology Meeting, Madison, WI, Jul. 21-25, 2001 (Abstract).

Yount et al. "Coronavirus Heterologous Gene Expression Vectors" Sixth Int'l Symposium on Positive Strand RNA viruses, Institute Pasteur, Paris France, May 28-Jun. 2, 2001 (Abstract).

Yount et al. "Rewiring the severe acute respiratory syndrome coronavirus (SARS-CoV) transcription circuit: Engineering a recombination-resistant genome" *PNAS* 103(33):12546-12551 (2006).

* cited by examiner

Virus titer $\log_{10}$ (PFU/ML) vs Hours Post-Infection

Legend:
- ◇ TGEV 1000
- ✕ TGEV 2N-1PflMI
- ○ TGEV ^3B 2N-1ScaI
- ○ TGEV SNEMp4A
- □ TGEV SNEM-1
- △ TGEV SNEM-4
- ✻ TGEV SNEM1 p15A
- ▽ TGEV SNEM4 p15A

PSEUDO E GENE FOR SNEM1 VIRUS?
ACAAAAC (SEQ ID NO:13)
25,275 → 25,287

SNEM1 AND 4 DELETION JUNCTION 25,832/833 – REMOVES E TSE SITE

E ATG START 25,857

← TGEV SNEM1
← TGEV SNEM4
← SNEM CLONE F

3A TSE ACTAAAC (SEQ ID NO:14)

S GENE — N GENE — 25,197 — M GENE — HP
E / 3B / E

ACTAAAC (SEQ ID NO:14) N TSE

TCTAAAC (SEQ ID NO:15)

StuI/PacI JUNCTION

ScaI AGTACT (SEQ ID NO:16)
25,813
25,157
N-TERMINAL ORF 3B DELETION

FIG. 9

VEE REPLICON PARTICLE-ENCODING TGEV E PROTEIN

C, E2, E1, REPLICON RNA

5'—[ TGEV ORF 1A & 1B | S | | M | N | ]—3'
GFP  ΔORF 3B/E  HP

↓ IN VITRO TRANSCRIPTION
↓ RNA TRANSFECTION

INFECTION →

VEE REPLICON → E PROTEIN → ASSEMBLY

TGEV REPLICON
TGEV S
GFP
TGEV M
TGEV N
TGEV HP

BHK CELL

RELEASE ←

INFECTIOUS TGEV REPLICON PARTICLES

TGEV REPLICON RNA
NUCLEOCAPSID
E PROTEIN
M GLYCOPROTEIN
S GLYCOPROTEIN

METHODS FOR PRODUCING RECOMBINANT CORONAVIRUS

RELATED APPLICATIONS

This application claims priority under 35 U.S.C. § 371 from PCT Application No. PCT/US02/12453, filed in English on Apr. 19, 2002, which claims the benefit of U.S. Application Ser. No. 60/285,320 and U.S. Application Ser. No. 60/285,318, both filed on Apr. 20, 2001, the disclosures and contents of which are incorporated by reference herein in their entireties.

STATEMENT OF FEDERAL SUPPORT

This invention was made possible with government support under grant numbers AI23946 and GM63228 from the National Institutes of Health. The United States government has certain rights to this invention.

FIELD OF THE INVENTION

The present invention relates to methods of producing recombinant nidovirus vectors, particularly coronavirus vectors, and expressing heterologous genes from said vectors.

BACKGROUND OF THE INVENTION

Transmissible gastroenteritis (TGE) is an economically important, acute enteric disease of swine, which is often 100% fatal in newborn piglets (Enjuanes, et al. (1995) *Dev. Biol. Stand.* 84:145-152; Enjuanes, et al. (1995) *Adv. Exp. Med. Biol.* 380:197-211; Laude, et al. (1990) *Vet. Microbiol.* 23:147-154). TGE virus (TGEV), the causative agent of TGE, is a member of the Coronaviridae family and the order Nidovirales. In addition to the Coronaviridae, the order Nidovirales also includes the Arteriviridae family, of which the swine pathogen porcine reproductive and respiratory syndrome virus (PRRSV) is a member (Cavanagh and Horzinek (1993) *Arch. Virol.* 128:395-396; de Vries, et al. (1997) *Semin. Virol.* 8:33-47; Siddell, et al. (1983) *J. Gen. Virol.* 64:761-776). Despite significant size differences (~13 to 32 kb), the polycistronic genome organization and regulation of gene expression from a nested set of subgenomic mRNAs are similar for all members of the order (de Vries, et al. (1997) *Semin. Virol.* 8:33-47; Snijder and Horzinek (1993) *J. Gen. Virol.* 74:2305-2316).

TGEV possesses a single-stranded, positive-sense ~28.5-kb RNA genome enclosed in a helical nucleocapsid structure that is surrounded by an envelope containing three viral proteins, including the S glycoprotein, the membrane (M) glycoprotein and a small envelope (E) protein (Eleouet, et al. (1995) *Virology* 206:817-822; Enjuanes and van der Zeijst (1995) In: S. G. Siddell (ed.), *The Coronaviridae*. Plenum Press, New York, N.Y., p. 337-376; Rasschaert and Laude (1987) *J. Gen. Virol.* 68:1883-1890; Risco, et al. (1996) *J. Virol.* 70:4773-4777). Remarkably, only the E and M proteins are absolutely required for particle formation, defining a novel model for virion budding (Fischer, et al. (1998) *J. Virol.* 72:7885-7894; Vennema, et al. (1996) *EMBO J.* 15:2020-2028). The TGEV genome contains eight large open reading frames (ORFs), which are expressed from full-length or subgenomic-length mRNAs during infection (Eleouet, et al. (1995) *Virology* 206:817-822; Sethna, et al. (1991) *J. Virol.* 65:320-325; Sethna, et al. (1989) *Proc. Natl. Acad. Sci. USA* 86:5626-5630). The 5'-most ~20 kb contains the replicase genes in two ORFs, 1A and 1B, the latter of which is expressed by ribosomal frameshifting (Almazan, et al. (2000) *Proc. Natl. Acad. Sci. USA* 97:5516-5521; Eleouet, et al. (1995) *Virology* 206:817-822). The 3'-most ~9 kb of the TGEV genome contains the structural genes, each preceded by a highly conserved transcription regulatory element (TSE) [ACTAAAC; SEQ ID NO:1]. The size of the functional TSE is subject to debate, but ranges from ~7-15+ nucleotides in length when analyzed in recombinant defective interfering RNAs (Enjuanes, et al. (2001) *J. Biotechnology* 88:183-204; Jeong, et al. (1996) *Virology* 217:311-322; Krishnan, et al. (1996) *Virology* 218:400-405; Joo and Makino (1995) *J. Virol.* 69:3339-3346). In general, TSE length affects the function of individual mutations because longer elements are generally more resistant to "debilitating" mutations (Enjuanes, et al. (2001) *J. Biotechnology* 88:183-204). As the leader RNA sequence is also defined by a TSE at its 3' end, some degree of base-pairing between the leader RNA and body TSE likely mediate virus transcription of subgenomic RNAs (Baker and Lai (1990) *EMBO J.* 9:4173-4179; Baric, et al. (1983) *J. Virol.* 48:633-640; Makino, et al. (1986) *Proc. Natl. Acad. Sci. USA* 83:4204-4208; Makino, et al. (1991) *J. Virol.* 65:6031-6041; Siddell, S. G. 1995. The coronaviridae, An introduction. In: The coronaviridae, eds. S. G. Siddell, Plenum Press, New York. pp 1-10). The subgenomic mRNAs are arranged in a co-terminal nested set structure from the 3' end of the genome, and each contains a leader RNA sequence derived from the 5' end of the genome. Although each mRNA is polycistronic, the 5'-most ORF is preferentially translated, necessitating the synthesis of a distinct mRNA species for each ORF (Lai and Cavanagh (1997) *Adv. Virus Res.* 48:1-100; McGoldrick, et al. (1999) *Arch. Virol.* 144:763-770; Sethna, et al. (1991) *J. Virol.* 65:320-325; Sethna, et al. (1989) *Proc. Natl. Acad. Sci. USA* 86:5626-5630). Both full-length and subgenomic-length negative-strand RNAs are also produced and have been implicated in mRNA synthesis (Baric and Yount (2000) *J. Virol.* 74:4039-4046; Sawicki and Sawicki (1990) *J. Virol.* 64:1050-1056; Schaad and Baric (1994) *J. Virol.* 68:8169-8179; Sethna, et al. (1991) *J. Virol.* 65:320-325; Sethna, et al. (1989) *Proc. Natl. Acad. Sci. USA* 86:5626-5630). Subgenomic RNA synthesis occurs by a method of discontinuous transcription, most likely by transcription attenuation during negative-strand synthesis (Baric and Yount (2000) *J. Virol.* 74:4039-4046; Sawicki and Sawicki (1990) *J. Virol.* 64:1050-1056).

The *coronavirus* E and M proteins function in virion assembly and release, which involve the constitutive secretory pathway of infected cells. Coexpression of the E and M proteins results in virus-like particle formation in cells, defining a novel, nucleocapsid-independent mechanism of enveloped-virus assembly (Vennema, et al. (1996) *EMBO J.* 15:2020-2028). The role of the E protein in virus assembly was further confirmed by reverse genetic analysis using targeted recombination (Fischer, et al. (1998) *J. Virol.* 72:7885-7894) and the development of TGEV replicon viruses (Curtis, et al. (2002) *J. Virol.* 76(3):1422-34). The TGEV M protein may serve to initiate the viral particle assembly process through interactions with genomic RNA and nucleoprotein in pre-Golgi compartments (Narayanan, et al. (2000) *J. Virol.* 74:8127-8134). The precise role of E in the assembly and release of *coronavirus* particles is not clear. Although an interaction between the E and M proteins has not yet been demonstrated, such an interaction likely occurs and would serve to facilitate the budding of viral particles. Additionally, E protein has been suggested to "pinch off the neck" of the assembled viral particles during the final stages of budding (Vennema, et al. (1996) *EMBO J.* 15:2020-2028).

PRRSV is endemic in most swine producing countries. Virions are enveloped 45-70 nm particles that contain 5 envelope proteins and an icosahedral nucleocapsid (N), which surrounds a single-stranded positive polarity RNA genome of about 15 kb (Pancholi, et al. (2000) *J. Infect. Dis.* 182:18-27; Pirzadeh and Dea (1998) *J. Gen. Virol.* 79:989-99). The 15 kDa N protein is most abundant and contains common conformational antigenic sites that are conserved of European and North American strains (Pirzadeh and Dea (1998) *J. Gen. Virol.* 79:989-99). N is likely multimerized to form icosahedral core structures (20-30 nm), which can be observed by EM. The major envelope proteins include a 25 kDa glycoprotein (GP5) and an 18-19 kDa unglycosylated M protein (Eleouet, et al. (1995) *Virology* 206:817-22; Meulenberg, et al. (1997) *Vet. Microbiol.* 55:197-202). GP5 (ORF 5) heterogeneity ranges from 50-90% amino acid identity among isolates, contains at least two neutralizing sites, and expression causes apoptosis (Eleouet, et al. (1995) *Virology* 206:817-22; Pirzadeh, et al. (1998) *Can. J. Vet. Res.* 62:170-7; Saif (1999) Transmissible gastroenteritis and porcine respiratory *coronavirus*, p. 295-325. In B. Straw, D'Allaire, S, Mengeling, W L and Taylor, D J (ed.), Diseases of Swine 8th edition. Iowa State University Press, Ames, Iowa; Tresnan, et al. (1996) *J. Virol.* 70:8669-74). The M protein (ORF6) contains 3 hydrophobic domains and accumulates in the ER of infected cells, where it forms disulfide-linked heterodimers with GP5 and may function in virus assembly (Meng (2000) *Vet. Microbiol.* 74:309-29). As with *equine arterivirus*, it is likely that coexpression of M and GP5 are needed for appropriate post-translational modification, folding and function, and for inducing high neutralizing antibody titers (Balasuriya, et al. (2000) *J. Virol.* 74:10623-30; Eleouet, et al. (1995) *Virology* 206:817-220).

Live, attenuated PRRSV vaccines causes viremia and may spread to other pigs. DNA immunization with a plasmid encoding GP5 of PRRSV induces specific neutralizing antibodies and reduces viremia and lung pathology in swine following challenge (Risco, et al. (1996) *J. Virol.* 70:4773-7). Recombinant adenovirus and vaccinia viruses encoding various PRRSV antigens are also being developed with encouraging results (Budzilowicz, et al. (1985) *J. Virol.* 53:834-40; Tresnan, et al. (1996) *J. Virol.* 70:8669-74). Several groups have concluded that effective PRRSV recombinant vaccines must induce high neutralizing titers, induce cellular immunity, induce heterotypic immunity and provide protection at mucosal surfaces (Eleouet, et al. (1995) *Virology* 206:817-22; Meulenberg, et al. (1997) *Vet. Microbiol.* 55:197-202). Achieving these goals is complicated by the generally low immunogenicity of the PRRSV envelope proteins and high genomic heterogeneity present in field isolates (Meulenberg, et al. (1997) *Vet. Microbiol.* 55:197-2020). Hence, improved vaccines are needed.

Recently, a simple and rapid approach for systematically assembling a full-length cDNA copy of the TGEV genomic RNA from which infectious transcripts can be produced has been described (Yount, et al. (2000) *J. Virol.* 74:10600-10611). This approach, as well as that of Almazan et al. ((2000) *Proc. Natl. Acad. Sci. USA* 97:5516-5521), will facilitate reverse genetic methods that impact all aspects of coronavirology, however, the production of infectious TGEV replicon particles is still limited.

SUMMARY OF THE INVENTION

A first aspect of the present invention is a helper cell for producing an infectious, replication defective, nidovirus particle. The helper cell comprises (a) a nidovirus permissive cell (e.g., a cell permissive of replication but not necessarily infection); (b) a nidovirus replicon RNA comprising the nidovirus packaging signal and a heterologous RNA sequence, wherein the replicon RNA further lacks a sequence encoding at least one nidovirus structural protein (e.g., lacks one, two, three, four or all); and (c) at least one separate helper RNA (e.g., one, two, three, four, etc. separate helper RNAs) encoding the at least one structural protein absent from the replicon RNA, the helper RNA(s) lacking the nidovirus packaging signal. The combined expression of the replicon RNA and the helper RNA in the nidovirus permissive cell produces an assembled nidovirus particle which comprises the heterologous RNA sequence, is able to infect a cell, and is unable to complete viral replication in the absence of the helper RNA due to the absence of the structural protein coding sequence in the packaged replicon.

Example nidoviruses that may be used to carry out the present invention include members of the familes Coronaviridae and Arteriviridae. Currently preferred are the coronaviruses.

In some embodiments, the replicon RNA further comprises a sequence encoding at least one of the nidovirus structural proteins (for example, the M, N, and/or S genes). In other embodiments, the replicon RNA lacks all of the nidovirus structural proteins. Thus in some embodiments, the helper RNA contains (or helper RNAs contain) at least one gene encoding a structural protein, such as the E, M, N, and/or S genes.

In certain preferred embodiments, the replicon RNA and/or the helper RNA contains at least one attenuating gene order rearrangement among the 3A, 3B, HP, S, E, M and N genes.

In certain embodiments, the helper RNA and/or the replicon RNA may include a promoter(in the helper RNA, to drive expression of the appropriate helper gene or genes; in the replicon RNA, to drive expression of the coronavirus genes or the heterologous genes (which may be driven by the same or a different promoter). In certain embodiments of the invention, the helper cell may include a heterologous DNA encoding the replicon RNA, and/or a heterologous DNA encoding the helper RNA, with the replicon RNA and/or the helper RNA being transcribed from the corresponding DNA in the permissive cell.

A further aspect of the present invention is a method of making infectious, replication defective, nidovirus particles, comprising: providing a helper cell as described above, producing the nidovirus particles in the helper cell; and then collecting the nidovirus particles from the helper cell. The replicon RNA and the at least one separate helper RNA are stably or transiently introduced into the helper cell by any suitable means, such as electroporation of the RNA into the cell, introduction of DNA into the cell as noted above, etc.

A still further aspect of the invention is infectious nidovirus particles containing a heterologous RNA within a replicon RNA as described above. Such particles may be produced by the methods described above. In certain preferred embodiments the present invention provides a composition comprising a population of infectious, replication defective, nidovirus particles, wherein each particle comprises a nidovirus replicon RNA, wherein the replicon RNA comprises a nidovirus packaging signal and one or more heterologous RNA sequences, wherein the replicon RNA further lacks a sequence encoding at least one nidovirus structural protein, and wherein the population contains no detectable replication-competent nidovirus particles as determined by passage on nidovirus permissive cells (e.g., cells permissive of infection and replication) in culture. As previously, the replicon RNA may further comprise a sequence encoding at least one nidovirus structural protein. Also as previously, the replicon RNA may contain at least one attenuating gene order rearrangement among the 3a, 3b, Hp, S, E, M and N genes.

A still further aspect of the present invention is a pharmaceutical formulation comprising infectious nidovirus particles as described above in a pharmaceutically acceptable carrier.

A still further aspect of the present invention is a method of introducing a heterologous RNA into a subject, comprising administering infectious nidovirus particles as described herein to the subject in an amount effective to introduce the heterologous RNA into the subject.

Nidovirus replicon RNAs and helper RNAs as described above, independent of the helper cell, are also an aspect of the present invention. Such RNAs may be provided in a suitable carrier such as an aqueous carrier for introduction into the helper cell as described above.

Further aspects of the present invention include DNAs encoding replicon RNAs or helper RNAs as described above, along with vectors and recombinant constructs carrying or comprising such DNA, all of which may be used to create the helper cells described above, and which may be provided in a suitable carrier such as an aqueous carrier for introduction into a helper cell as described above.

The foregoing and other objects and aspects of the present invention are explained in detail in the specification set forth below.

BRIEF DESCRIPTION OF THE DRAWINGS

Figure 3C:
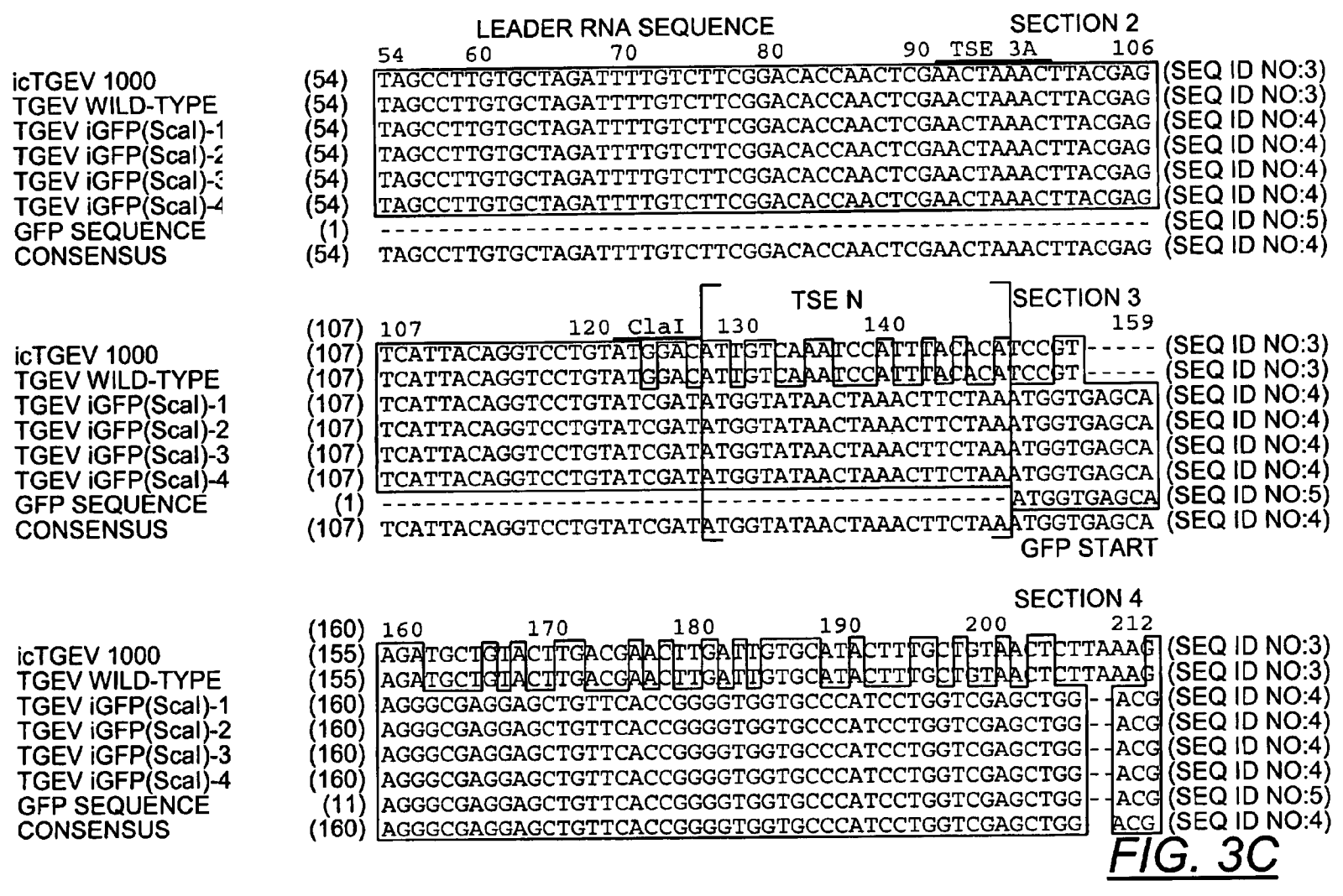

FIG. 3C shows the sequence of the leader-containing GFP transcripts which originate from the 3A TSE site. In this context, the 21-nucleotide N TSE site is not recognized as an initiator of subgenomic transcription.

FIG. 6 shows recombinant virus growth. Viruses were inoculated into ST cells. Note that the TGEV SNEMp4A isolate was not robust and was isolated at passage 4 after the initial transfection of full-length SNEM transcripts into cells. In contrast, TGEV SNEM-1 and SNEM-4 viruses were plaque purified from passage 9 following transfection. TGEV SNEM1 p15A and SNEM4 p15A were isolated following 15 serial passages of TGEV SNEM 1 and 4 viruses in ST cells, respectively, and despite N rearrangement replicate to titers approaching that of wild-type virus.

FIG. 7 shows the sequence of the RT-PCR leader-containing N transcripts (TXPT). TGEV SNEM1 leader-containing N transcripts were sequenced. Five of seven N transcripts initiated from the 3A TSE site and two initiated from the N TSE site.

FIG. 8 graphically depicts the genetic organization of TGEV SNEM 1 and 4. The TGEV F domain was cloned from TGEV SNEM1 and SNEM4 infected cells. The major alteration was a deletion of residual ORF 3B sequences in the original SNEM Clone F sequence. Note that the E TSE site at position 25,813 is deleted in the TGEV SNEM1 and 4 viruses.

FIG. 9 depicts the strategy to assemble TGEV-Rep(AvrII) VRPs. In the full-length TGEV-Rep(AvrII) cDNA construct, ORF 3A has been replaced with GFP, and ORF 3B and the 5' end of the E gene have been deleted. To produce packaged replicon particles, replicon RNA-transfected cells were infected with VEE VRPs expressing the TGEV E protein [VEE-TGEV(E)]. Alternatively, TGEV-Rep(AvrII) replicon RNAs can be co-electroporated with pVR21-E1-derived transcripts. TGEV VRPs should be released from cells that can be used as single-hit expression vectors.

FIG. 10 shows the growth kinetics of wild-type (WT) TGEV alone and TGEV with VEE VRPs expressing a $G_1$ Norwalk-like virus capsid (WT+VEE).

FIG. 11A shows RT-PCR products of GFP transcripts derived from cells transfected with TGEV VRPs (lane 1). A 1-kb ladder is shown in lane 2. Arrow indicates leader-containing GFP amplicon.

FIG. 11B shows RT-PCR products of N and M subgenomic transcripts derived from cells transfected with TGEV VRPs. A 1-kb ladder is shown in lane 1. Arrows indicate leader-containing M (lane 2) or N (lane 3) amplicons.

FIG. 12 shows the growth kinetics of TGEV replicon. Plaque assays were performed on TGEV-GFP2 (closed diamond) and TGEV VRP (closed square)-infected cultures.

DETAILED DESCRIPTION OF PREFERRED EMBODIMENTS

Figure 1A:
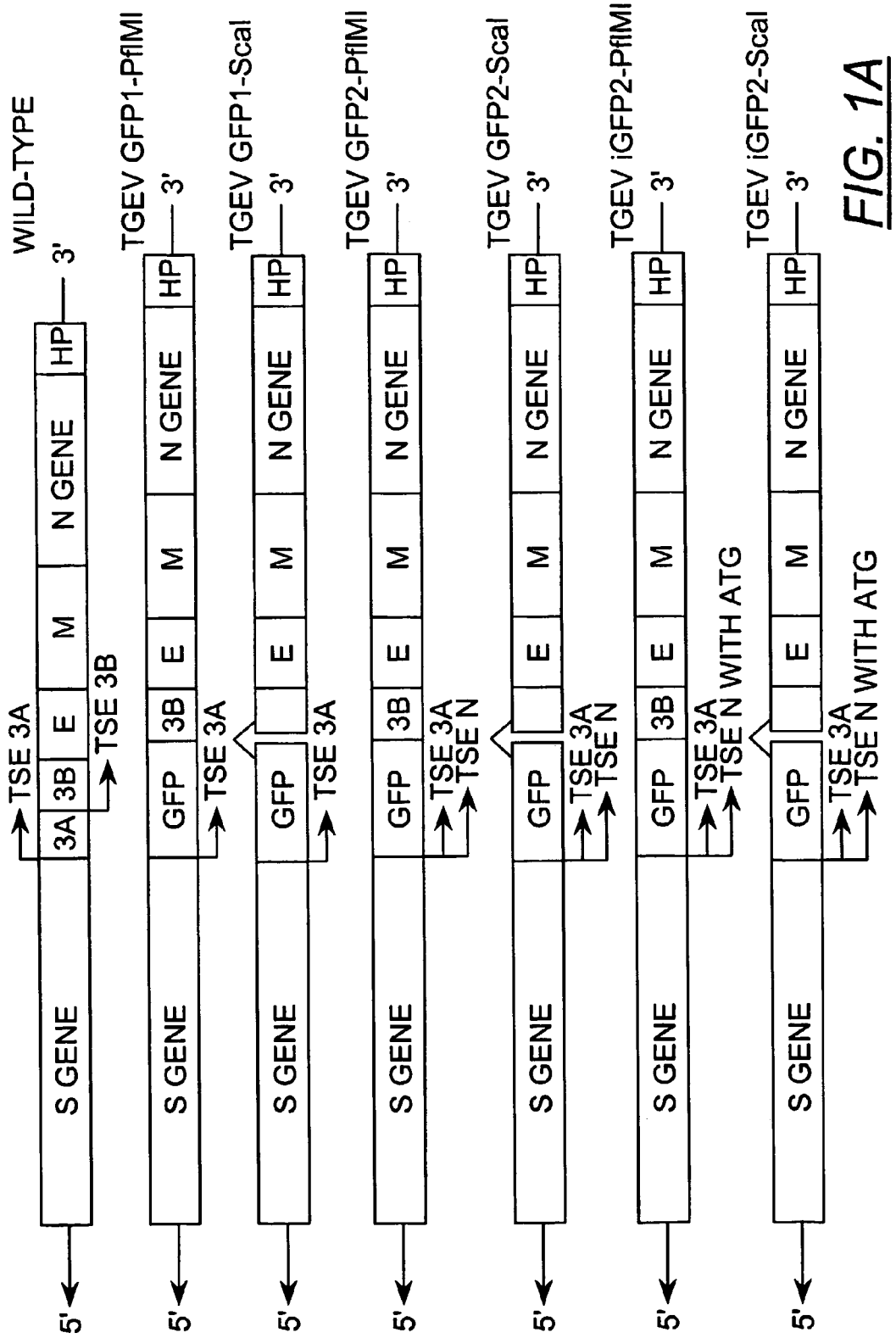
FIG. 1A shows the organization of TGEV recombinant viruses encoding GFP. TGEV ORF 3A and 3A and a portion of 3B were removed and replaced with GFP under control of the 3A and N TSE.

"Nidovirus" as used herein refers to viruses within the order Nidovirales, including the families Coronaviridae and Arteriviridae. All viruses within the order Nidovirales share the unique feature of synthesizing a nested set of multiple subgenomic mRNAs. See M. Lai and K. Holmes, *Coronaviridae: The Viruses and Their Replication*, in Fields Virology, pg 1163, (4$^{th}$ Ed. 2001). Particular examples of Coronaviridae include, but are not limited to, toroviruses and coronaviruses.

"*Coronavirus*" as used herein refers to a genus in the family Coronaviridae, which family is in turn classified within the order Nidovirales. The coronaviruses are large, enveloped, positive-stranded RNA viruses. They have the largest genomes of all RNA viruses and replicate by a unique mechanism which results in a high frequency of recombination. The coronaviruses include antigenic groups I, II, and III. While the present invention is described primarily with respect to porcine transmissible gastroenteritis virus (TGEV), the invention may be carried out with any coronavirus, such as human respiratory coronavirus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine *coronavirus*, avian infectious bronchitis virus, and turkey *coronavirus*. See generally M. Lai and K. Holmes, *Coronaviridae: The Viruses and Their Replication*, in Fields Virology, (4$^{th}$ Ed. 2001).

A "nidovirus permissive cell" as used herein can be any cell in which a *coronavirus* can at least replicate, including both naturally occurring and recombinant cells. In some embodiments the nidovirus permissive cell is also one which the nidovirus can infect. The nidovirus permissive cell may be one which has been modified by recombinant means to express a cell surface receptor for the nidovirus A "replicon RNA" as used herein refers to RNA that is packaged into *coronavirus* particles within a helper cell. The replicon RNA may be introduced into the helper cell by any suitable means, including but not limited to electroporation of the RNA, transient or stable transfection of the helper cell with a DNA that transcribes the replicon RNA, etc.

A "helper RNA" as used herein refers to an RNA that encodes a structural protein absent from a corresponding replicon RNA. The helper RNA may be introduced into the helper cell by any suitable means, including but not limited to electroporation of the RNA, transient or stable transfection of the helper cell with a DNA that transcribes the helper RNA, etc.

A "heterologous RNA" as described herein may encode anything which it is desired to administer into a subject for any purpose. For example, the heterologous RNA may encode, and express in the subject, a protein or peptide. The protein or peptide may, for example, be an antigen or immunogen, for example where it is desired to raise antibodies in an animal subject, which antibodies can be collected and used for diagnostic or therapeutic purposes, or where it is desired to elicit an immune response to the protein or peptide in subject for producing at least a partial protective immune response to the protein or peptide in the subject.

A "structural protein" as used herein refers to a protein required for production of viral particles, such as those encoded by the S, E, M and N genes. Where replicon or helper RNAs lack sequences encoding the structural protein, the sequences may be wholly or partly deleted, so long as the sequence is effectively incapable of producing the necessary protein in functional form.

"Replication defective" as used herein means that the viral genome contained within viral particles produced by the present invention cannot of themselves produce new viral particles.

Subjects which may be administered or treated by the viral particles or VLPs of the present invention may be any subject, generally vertebrates, for which the viral particles or VLPs are infectious, including but not limited to birds and mammals such as pigs, mice, cows, and humans).

While the invention is sometimes described with particular reference to coronaviruses and TGEV below, it will be understood that this teaching is applicable to other nidoviruses and its families (as described above) as well.

The present invention may be implemented in any of a varieties of ways, including by techniques, compositions and formulations known in the art (see, e.g., U.S. Pat. No. 6,156,558 to Johnston et al.; U.S. Pat. No. 5,639,650 to Johnston et al.) modified in light of the teaching set forth above and below. Applicants specifically intend that the disclosures of all United States patent references cited herein be incorporated herein by reference in their entirety.

The present invention describes the assembly of recombinant transmissible virus and replicons that express heterologous genes which can be used to make vaccines against homologous and heterologous pathogens (Agapov, et al. (1998) *Proc. Natl. Acad. Sci. USA* 95:12989-12994; Balasuriya, et al. (2000) *J. Virol.* 74:10623-10630; Berglund, et al. (1998) *Nat. Biotechnol.* 16:562-565; Bredenbeek, et al. (1993) *J. Virol.* 67:6439-6446; DiCiommo and Bremner (1998) *J. Biol. Chem.* 273:18060-18066; Dollenmaier, et al. (2001) *Virology* 281:216-230; Dubensky, et al. (1996) *J. Virol.* 70:508-519; Hevey, et al. (1998) *Virology* 251:28-37; Johanning, et al. (1995) *Nucleic Acids Res.* 23:1495-1501; Khromykh (2000) *Curr. Opin. Mol. Ther.* 2:555-569; Khromykh and Westaway (1997) *J. Virol.* 71:1497-1505; Liljestrom and Garoff (1991) *Bio/Technology* 9:1356-1361; Percy, et al. (1992) *J. Virol.* 66:5040-5046; Porter, et al. (1993) *J. Virol.* 67:3712-3719; Pushko, et al. (2000) *Vaccine* 19:142-153; Schultz-Cherry, et al (2000) *Virology* 278:55-59; Varnavski and Khromykh (1999) *Virology* 255:366-375; Varnavski, et al. (2000) *J. Virol.* 74:4394-4403).

The use of replicons as a vaccine delivery system offers a number of important advantages over the use of live, attenuated virus vaccines, which are capable of independent spread and recombination with wild-type virus populations. Replicon vectors are an inherently safer alternative to the use of live, attenuated virus vaccines due to the lack of progeny virus production. In addition, high-level expression of heterologous genes can result in the use of a relatively low dose of virus replication particles (VRPs) for vaccination and inmmune induction. Moreover, gene order rearranged viruses will be inherently more stable and less pathogenic than attenuated wild-type strains.

*Coronavirus* vectors such as TGEV vectors provide a system for the incorporation and expression of one or more foreign genes, as *coronaviruses* contain a polycistronic genome organization and synthesize multiple subgenomic-length mRNAs (Enjuanes and van der Zeijst (1995) In: S. G. Siddell (ed.), *The Coronaviridae*. Plenum Press, New York, N.Y., p. 337-376). It has been shown that TGEV ORFs 3A and 3B likely encode luxury functions that can be deleted without affecting infectivity or replication in vitro and may serve as appropriate sites for the insertion of heterologous genes into the genome (Enjuanes and van der Zeijst (1995) In: S. G. Siddell (ed.), *The Coronaviridae*. Plenum Press, New York, N.Y., p. 337-376; Laude, et al. (1990) *Vet. Microbiol.* 23:147-154; McGoldrick, et al. (1999) *Arch. Virol.* 144:763-770; Vaughn, et al. (1995) *J. Virol.* 69:3176-3184; Wesley, et al. (1991) *J. Virol.* 65:3369-3373). In contrast to *arteriviruses*, the *coronavirus* transcription start elements (TSEs) rarely overlap, or overlap slightly, with upstream ORFs, simplifying the design and expression of foreign genes from downstream TSEs (Chen, et al. (1995) *Virus Res.* 38:83-89; Eleouet, et al. (1995) *Virology* 206:817-822; Tung, et al. (1992) *Virology* 186:676-683). The helical nucleocapsid structure of *coronaviruses* such as TGEV also minimize packaging constraints and allow for the expression of multiple large genes from a single construct (Enjuanes and van der Zeijst (1995) In: S. G. Siddell (ed.), *The Coronaviridae*. Plenum Press, New York, N.Y., p. 337-376; Lai and Cavanagh (1997) *Adv. Virus Res.* 48:1-100; Risco, et al. (1996) *J. Virol.* 70:4773-4777). Importantly, recombinant *coronavirus* VRPs can be readily targeted to other mucosal surfaces mammalian species such as swine by simple replacements in the S glycoprotein gene, which has been shown to determine tissue and species tropism (Delmas, et al. (1992) *Nature* 357:417-420; Kuo, et al. (2000) *J. Virol.* 74:1393-1406; Sánchez, et al. (1999) *J. Virol.* 73:7607-7618; Tresnan, et al. (1996) *J. Virol.* 70:8669-8674). For these reasons, *coronavirus* VRPs and vectorsprovide a valuable approach for the production of combination vaccines in a variety of mammalian hosts.

Accordingly, one aspect the present invention relates to a method for inducing an antigenic and/or immunological response in a vertebrate to a pathogen by inoculating the vertebrate with a recombinant *coronavirus* virus modified by the presence, in a nonessential region of the coronavirus genome, of nucleic acid from any source which encodes for and expresses an antigen of the pathogen, or a protein or peptide for which an antibody is desired.

In a further aspect, the present invention is directed to a method for expressing a gene product or inducing an antigenic or immunological response to an antigen in a vertebrate with a recombinant virus which does not productively replicate in the cells of the vertebrate but which does express the gene product or the antigen in those cells.

The methods can comprise inoculating the vertebrate with the recombinant virus, e.g., by introducing the virus into the vertebrate subcutaneously, intradermally, intramuscularly, orally or in ovum.

The antigen or antigenic protein or peptide encoded by the heterologous RNA and expressed in the host can be an antigen of a vertebrate pathogen, e.g., a mammalian pathogen or a swine pathogen, such as a rabies G antigen, gp51, 30 envelope antigen of bovine leukemia virus, FeLV envelope antigen of feline leukemia virus, glycoprotein D antigen of herpes simplex virus, a fusion protein antigen of the Newcastle disease virus, an RAV-1 envelope antigen of rous associated virus, nucleoprotein antigen of avian or mammalian influenza virus, a fusion protein antigen of porcine reproductive and respiratory disease virus (PRRSV), a matrix antigen of the infectious bronchitis virus, a glycoprotein species of PRRSV or a peplomer antigen of the infectious brochitis virus.

In another aspect, the present invention is directed to synthetic recombinant *coronavirus* modified by the insertion therein of DNA or RNA from any source, and particularly from a non-*coronavirus* or non-TGEV source, into a nonessential region of the TGEV genome. Synthetically modified TGEV virus recombinants carrying exogenous (i.e. non-coronavirus) nucleic acids or genes encoding for and expressing an antigen, which recombinants elicit the production by a vertebrate host of immunological responses to the antigen, and therefore to the exogenous pathogen, are used according to the invention to create novel vaccines which avoid the drawbacks of conventional vaccines employing killed or attenuated live organisms, particularly when used to inoculate vertebrates.

Figure 1B:
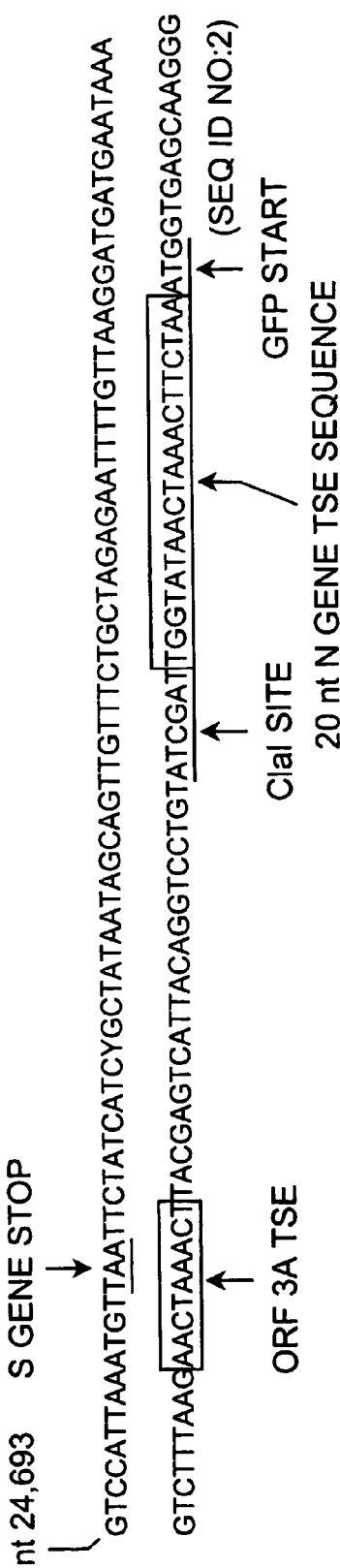
FIG. 1B shows the sequence organization of GFP in FiGFP2(PflMI) (SEQ ID NO:2). GFP was inserted downstream of the ORF 3A TSE. The TGEV sequence originating at the 3' end of the S gene through the start of the GFP gene is shown, and the important TSEs and restriction sites are labeled.

The present invention demonstrates that the Green Fluorescent Protein (GFP) and the PRRSV surface glycoprotein (GP5) can be inserted and expressed from the TGEV genome, demonstrating the feasibility of using TGEV-based replicon vectors for heterologous gene expression. Efficient self-replication of in vitro-transcribed recombinant TGEV and replicon RNAs was demonstrated by GFP expression, the presence of leader-containing subgenomic transcripts, and the production of infectious recombinant virus and VRPs. These data support previous results suggesting that the TGEV ORFs 3A and 3B were not required for virus replication in vitro, although these genes may confer subtle fitness advantages that cannot be detected by these assays (Laude, et al. (1990) *Vet. Microbiol.* 23:147-154; McGoldrick, et al. (1999) *Arch. Virol.* 144:763-770; Wesley, et al. (1991) *J. Virol.* 65:3369-3373). It should also be possible to determine the minimal TGEV replicon size by serially deleting each of the downstream ORFs. However, this may be complicated by the requirement of RNA secondary structures that may be essential for genome replication or subgenomic RNA synthesis (Hsue, et al. (2000) *J. Virol.* 74:6911-6921; Hsue, et al. (1997) *J. Virol.* 71:7567-7578; Williams, et al. (1999) *J. Virol.* 73:8349-8355). As has been previously reported, efficient TGEV RNA transfection and expression in cells were significantly enhanced upon the co-electroporation of N transcripts (Wesley, et al. (1991) *J. Virol.* 65:8349-8355). Because the nucleocapsid protein interacts with leader and negative-strand RNA and colocalizes with the viral polymerase sites of RNA synthesis, it is possible that the N protein may function as part of the transcription complex in some undetermined manner (Baric, et al. (1988) *J. Virol.* 62:4280-4287; Denison, et al. (1999) *J. Virol.* 73:6862-6871). Replicon constructs containing N gene deletions may facilitate studies of the possible N gene function(s) in TGEV replication. Using synthetic defective-interfering (DI) RNA genomes, some groups have reported that downstream TSEs suppress transcription from upstream TSEs (Joo and Makino (1995) *J. Virol.* 69:272-280; Krishnan, et al. (1996) *Virology* 218:400-405). In addition, data suggest that the N gene TSE is the strongest initiator of TGEV subgenomic RNA transcription (Hiscox, et al. (1995) *Virus Res.* 36:119-130; Jacobs, et al. (1986) *J. Virol.* 57:1010-1015). In the recombinant virus and replicon RNAs described herein, GFP subgenomic mRNA synthesis was initiated from the normal ORF 3A TSE rather than from the 20-nt N gene TSE that has been duplicated just upstream of gfp (FIG. 1B). The results presented herein do not necessarily contradict earlier reports, as in this context the N gene TSE function was silent and would not display the reported phenotypes. Also, fundamental differences exist between the two systems used in these analyses (DI versus nearly full-length replicon), including the rapid replication of small ~2- to 3-kb DI RNAs and TSE presentation, compared with 28.5-kb genome-length RNAs. For example, experiments utilizing DI systems involved TSE elements within primary and secondary flanking genome sequence contexts that were not authentic, while the TSEs in the recombinant viruses and replicons presented herein closely approximate the wild-type TGEV genome. These data suggest that TSE location and flanking sequences likely have an impact on gene expression, especially in promoter proximal locations, which are fundamentally different in the two systems. The simplest interpretation of these data is that the random insertion of a large ~20-nt TSE element is not sufficient to initiate TGEV subgenomic mRNA synthesis unless this TSE is provided to the viral transcriptional machinery in an appropriate context that as of yet remains unknown. These data, as well as that obtained concerning bovine *coronavirus* (Pancholi, et al. (2000) *J. Infect. Dis.* 182:18-27), has lead to the hypothesis that TGEV subgenomic RNA transcription may be mediated by long-range RNA and/or ribonucleoprotein interactions, which are most definitely dependent on higher orders of genome structure.

Smaller leader-containing RNAs were noted in the present invention, indicating the presence of cryptic transcription start sites within GFP. This phenomenon was previously observed following expression of GFP from the MHV genome (Fischer, et al. (1997) *J. Virol.* 71:5148-5160; Schaad and Baric (1993) *Virology* 196:190-198). Both the TGEV and MHV genomes contain a number of atypical start sites that result in the transcription of aberrant subgenomic RNAs (Fischer, et al. (1997) *J. Virol.* 71:5148-5160). These data further substantiate the conclusion that the insertion of TSE elements may not be enough to direct TGEV subgenomic mRNA synthesis and that genome location, flanking sequence, and secondary sequence likely function in this process.

The SNEM viruses and their revertants provided in the present invention will also provide new opportunities for the development of safe and effective *coronavirus* vaccines and heterologous expression vectors. Gene order mutants and their revertant viruses will likely be attenuated in animals, but allow for high level expression of foreign genes (Wertz, et al. (1998) *Proc. Natl. Acad. Sci. USA* 95:3501-3506). It is believed that recombination with wild-type strains may result in attenuated progeny, either from the gene order rearrangement, or from the compensatory mutations, which will likely enhance TGEV SNEM virus replication, but prove detrimental to wild-type TGEV virus fitness and replication.

The VEE, Kunjin, and *Sindbis* replicon packaging systems involve the co-transfection of replicon and helper RNAs that express the structural genes (Pushko, et al. (1997) *Virology* 239:389-401). In addition to this method, replicon RNAs have been packaged by the expression of structural genes in trans from wild-type or mutated virus (Nugent, et al. (1999) *J. Virol.* 73:427-435; Percy, et al. (1992) *J. Virol.* 66:5040-5046). An important concern with these types of replicon systems is the production of recombinant virus, especially when considering the development of a replicon particle vaccine. Recombinant viruses have been isolated from *Sindbis* virus and VEE virus replicon systems that may be the result of recombination between replicon and helper RNAs and/or co-packaging of replicon and helper RNAs into the same VRP (Frolov, et al. (1997) *J. Virol.* 71:2819-2829; Geigenmuller-Gnirke, et al. (1991) *Proc. Natl. Acad. Sci. USA* 88:3253-3257; Pushko, et al. (1997) *Virology* 239:389-401). *Coronaviruses* undergo homologous recombination at high frequencies during mixed infection, which presents a significant concern for the production and use of TGEV replicons (Baric, et al. (1990) *Virology* 177:646-656; Fu and Baric (1992) *Virology* 189:88-102; Mendez, et al. (1996) *Virology* 217:495-507). The *coronavirus* replicon packaging system of the present invention involves, in one embodiment, the use of an unrelated virus vector (VEE). In one embodiment of this system, *coronavirus*-Rep(AvrII) RNAs were packaged by the expression of TGEV E in trans from VEE VRPs as well as from pVR21-E1-derived helper RNA transcripts. Because the TGEV replicon packaging system involves the use of an unrelated virus vector (VEE), the possibility of a recombination event between replicon and helper RNAs may be reduced. In addition, the TGEV E gene carried in the VEE replicon construct lacks an appropriate TSE, which was necessary for the initiation of subgenomic RNA transcription. As this same TSE was deleted in the TGEV-Rep(AvrII) construct, expression of TGEV helper genes that are recombined into TGEV replicon RNAs should be minimized in this system. Although recombinant wild-type TGEV was not detected, this concern could also be reduced by the inclusion of attenuating mutations in the helper proteins and/or the engineering of a bipartite replicon and helper system (TGEV E and M structural proteins) (Pushko, et al. (1997) *Virology* 239:389-401). Nevertheless, the possibility of RNA recombination between the replicon RNA and wild-type virus cannot be eliminated and remains an important issue requiring additional analysis.

VEE replicon vectors may be used to express *coronavirus* structural genes in producing combination vaccines. Dendritic cells, which are professional antigen-presenting cells and potent inducers of T-cell responses to viral antigens, are preferred targets of VEE and VRP infection, while TGEV targets the mucosal surfaces of the respiratory and gastrointestinal tract (Bancherau and Steinman (1998) *Nature* 392:245-252; Enjuanes, et al. (1995) *Dev. Biol. Stand.* 84:145-152; Enjuanes and van der Zeijst (1995) In: S. G. Siddell (ed.), *The Coronaviridae*. Plenum Press, New York, N.Y., p. 337-376; MacDonald and Johnston (2000) *J. Virol.* 74:914-922). As the VEE and TGEV replicon RNAs synergistically interact, two-vector vaccine systems are feasible that may result in increased immunogenicity when compared with either vector alone. Combination prime-boost vaccines (e.g., DNA immunization and vaccinia virus vectors) have dramatically enhanced the immune response (notably cellular responses) against target papillomavirus and lentivirus antigens compared to single-immunization regimens (Chen, et al. (2000) *Vaccine* 18:2015-2022; Gonzalo, et al. (1999) *Vaccine* 17:887-892; Hanke, et al. (1998) *Vaccine* 16:439-445; Pancholi, et al. (2000) *J. Infect. Dis.* 182:18-27). Using different recombinant viral vectors (influenza and vaccinia) to prime and boost may also synergistically enhance the immune response, sometimes by an order of magnitude or more (Gonzalo, et al. (1999) *Vaccine* 17:887-892). The strategy presented herein for the assembly of TGEV replicon constructs was based on the use of six cDNA subclones that span the entire length of the TGEV genome, designated fragments A, B 1, B2, C, D/E, and F (Yount, et al. (2000) *J. Virol.* 74:10600-10611). Each fragment is flanked by restriction sites that leave unique interconnecting junctions of 3 or 4 nt in length (BglI and BstXI). These sticky ends are not complementary to most other sticky ends generated with the same enzyme at other sites in the DNA, allowing for the systematic assembly of TGEV cDNAs by in vitro ligation.

This strategy is capable of circumventing problems associated with genome size constraints as well as regions of chromosomal instability, while allowing for simple reverse genetic applications. In this application, the full-length TGEV cDNA constructs must be synthesized de novo and do not exist intact in bacterial vectors, circumventing problems with sequence instability. However, this did not restrict the applicability of this approach. In fact, the separation of the replicon constructs into distinct fragments allows for genetic manipulation of independent subclones, thereby minimizing the occurrence of spurious mutations that arise during recombinant DNA manipulation. Because replicon cDNAs are consumed during in vitro transcription in this strategy, a weakness of this approach is that the full-length replicon cDNAs are consumed with use and must be continually rebuilt. However, replicon cDNAs will likely be stable in bacterial artificial chromosome vectors after reverse genetic manipulations, preventing the need for repetitive de novo synthesis by engineered constructs (Almazan, et al. (2000) Proc. Natl. Acad. Sci. USA 97:5516-5521; Messerle, et al. (1997) Proc. Natl. Acad. Sci. USA 94:14759-14763).

The synthesis of large RNA transcripts (~27 to 29 kb) in vitro is problematic, and the electroporation of such large RNA constructs, even in the presence of enhancing N transcripts, has also proven difficult, resulting in a 1% transfection efficiency. Therefore, transfecting cells with helper packaging constructs and subsequently passing the *coronavirus* VRPs in the presence of VEE-TGEV(E) VRPs can address this issue. In this way, VRPs can be amplified and high concentrations may amplify replicon titers for future applications. In addition, the use of a DNA launch platform, such as with a *cytomegalovirus* promoter, may be used to overcome any problems associated with an RNA launch system.

Helper or replicon RNAs (and their corresponding DNAs) that contain two or more genes optionally but preferably include a gene order rearrangement to atttenuate (e.g., reduce the virulence) as compared to a corresponding wild-type virus that did not contain such a gene order rearrangment (i.e., comparing a virus with all of the genes and the order rearrangement with a wild-type virus). Depending upon the number of genes within the helper or replicon RNA, it may contain two, three, or four or more gene order rearrangements. The wild-type order is reflected in the first transcript shown in FIG. 1A, and is, from 5' to 3', the gene order of: S, 3A, 3B, E, M, N, and HP. For example, modified orders for the replicon RNA, when the helper RNA contains the E gene, may include: S, 3B, M, N, HP and 3A; 3A, 3B, M, N, HP and S; S, 3A, 3B, N, Hp, and M; etc. In other embodiments, the E gene may be provided alone on the replicon RNA, and the helper RNA may contain the genes described above in the orders given above. Modified orders for the replicon RNA, when the helper RNA contains the M and N (in natural or reverse order) genes, may include: 3A, 3B, E, S and HP; S, E, 3A, 3B, and HP; S, 3A, 3B, E, and HP; S, E, HP, 3A, and 3B, etc. In other embodiments, the replicon RNA may contain the M and N genes (in natural or reverse orders), and the remaining genes may be provided on the helper RNA in orders such as given above. In still other embodiments, where the helper RNA contains the S gene, the replicon RNA may contain the remaining genes in the order 3B 3A, E, M, N, and HP; 3A, 3B, E, N, M, and HP; 3B, 3A, E, N, M, and HP; etc. Again, the replicon RNA may contain the S gene, and the helper RNA may contain the remaining genes in the orders given above. The 3A, 3B, and HP genes are nonessential and some or all may be deleted, or they may be included in an alternate order to serve as attenuating mutations. The genes may be divided among multiple helper RNAs, some or all of which contain gene order rearrangements. The foregoing examples are merely illustrative, and numerous additional variations will be readily apparent to those skilled in the art.

In other embodiments, an attenuating mutation can be introduced by deleting one or more of the nonessential genes 3A, 3B, and HP.

The infectious, replication defective, nidovirus particles may be prepared according to the methods disclosed herein in combination with techniques known to those skilled in the art. The method includes transfecting an nidovirus-permissive cell with a replication defective replicon RNA including the nidovirus packaging segment and an inserted heterologous RNA, a first helper RNA including RNA encoding at least one nidovirus structural protein, and a second helper RNA including RNA encoding at least one nidovirus structural protein which is different from that encoded by the first helper RNA; producing the nidovirus particles in the transfected cell; and collecting the nidovirus particles from the cell. The step of transfecting the nidovirus-permissive cell can be carried out according to any suitable means known to those skilled in the art. For example, uptake of the RNA into the cells can be achieved by any suitable means, such as for example, by treating the cells with DEAE-dextran, treating the cells with "LIPOFECTIN™", and by electroporation, with electroporation being the currently preferred means of achieving RNA uptake into the nidovirus-permissive cells. These techniques are well known in the art. See e.g., U.S. Pat. No. 5,185,440 to Davis et al., and PCT Publication No. WO 92/10578 to Bioption A B, the disclosures of which are incorporated herein by reference in their entirety.

The step of producing the infectious viral particles in the cells may also be carried out using conventional techniques. See e.g., U.S. Pat. No. 5,185,440 to Davis et al., PCT Publication No. WO 92/10578 to Bioption A B, and U.S. Pat. No. 4,650,764 to Temin et al. (although Temin et al., relates to retroviruses rather than nidoviruses). The infectious viral particles may be produced by standard cell culture growth techniques.

The step of collecting the infectious nidovirus particles may also be carried out using conventional techniques. For example, the infectious particles may be collected by cell lysis, or collection of the supernatant of the cell culture, as is known in the art. See e.g., U.S. Pat. No. 5,185,440 to Davis et al., PCT Publication No. WO 92/10578 to Bioption A B, and U.S. Pat. No. 4,650,764 to Temin et al. (although Temin et al. relates to retroviruses rather than nidoviruses). Other suitable techniques will be known to those skilled in the art. Optionally, the collected infectious nidovirus particles may be purified if desired. Suitable purification techniques are well known to those skilled in the art.

Pharmaceutical formulations, such as vaccines or compositions for producing antibodies in animals of the present invention comprise an antigenic or immunogenic amount of the infectious, replication defective nidovirus particles as disclosed herein in combination with a pharmaceutically acceptable carrier. An "antigenic amount" is an amount of the nidovirus particles which is sufficient to evoke the production of antibodies to the encoded antigenic protein or peptide contained and expressed on the heterologous RNA. An "immunogenic amount" is an amount of the infectious nidovirus particles which is sufficient to evoke an immune response in the subject to which the pharmaceutical formulation is administered. An amount of from about $10^3$, $10^5$ or $10^7$ to about $10^{10}$ or $10^{12}$ plaque forming units per dose is believed suitable, depending upon the age and species of the subject being treated, and the purpose of the treatment. Exemplary pharmaceutically acceptable carriers include, but are not limited to, sterile pyrogen-free water and sterile pyrogen-free physiological saline solution. Subjects which may be administered immunogenic amounts of the infectious, replication defective nidovirus particles of the present invention include but are not limited to human and animal (e.g., horse, donkey, mouse, hamster, monkeys) subjects. Administration may be by any suitable means, such as intraveneous, intraperitoneal or intramuscular injection.

The examples, which follow, are set forth to illustrate the present invention, and are not to be construed as limiting thereof. In the following examples, mM means millimolar, μg means microgram, ml means milliliter, μl means microliter, V means volt, μF means microfarad, cm means centimeter, h means hour, ORF means open reading frame, GFP means green fluorescent protein, PBS means phosphate-buffered saline, M means molar, s means second, nt means nucleotide, and min means minute.

EXAMPLE 1

Virus and Cells

The Purdue strain of TGEV (ATCC VR-763) was obtained from the American Type Culture Collection and passaged once in swine testicular (ST) cells. ST cells were obtained from the American Type Culture Collection (ATCC 1746-CRL) and maintained in minimal essential medium containing 10% fetal clone II (HyClone Laboratories, Inc., Logan, Utah) and supplemented with 0.5% lactalbumin hydrolysate, 1× nonessential amino acids, 1 mM sodium pyruvate, kanamycin (0.25 μg/ml), and gentamicin (0.05 μg/ml). Baby hamster kidney (BHK) cells (BHK-21 [ATCC CCL10]) were maintained in alpha-minimal essential medium containing 10% fetal calf serum supplemented with 10% tryptose phosphate broth, kanamycin (0.25 μg/ml), and gentamicin (0.05 μg/ml). To determine the effect of co-infection with TGEV and VEE VRPs on TGEV growth rate, cultures of ST cells ($5 \times 10^5$) were infected with wild-type TGEV alone or with wild-type TGEV and VEE VRPs encoding a Norwalk-like virus (VEE-NCFL) capsid antigen (ORF 2) at a multiplicity of infection (MOI) of 5 for 1 h (Harrington, et al. (2002) *J. Virol.* 76:730-742). The cells were washed twice with phosphate-buffered saline (PBS) to remove residual virus and VEE VRPs, and the cells were subsequently incubated at 37° C. in complete medium. At different times post-infection, progeny virions were harvested and assayed by plaque assay in ST cells, as previously described (Yount, et al. (2000) *J. Virol.* 74:10600-10611).

EXAMPLE 2

Recombinant DNA Manipulations of TGEV F Subclone

Plasmid DNAs were amplified in *Escherichia coli* DH5α and purified with the QIAprep Miniprep kit (Qiagen Inc., Valencia, Calif.). All enzymes were purchased from New England BioLabs (Beverly, Mass.) and used according to the manufacturer's directions. DNA fragments were isolated from Tris-acetate-EDTA agarose gels (0.8%) with the QIAEX II gel extraction kit (Qiagen Inc.). All DNA was visualized using Dark Reader technology (Clare Chemical Research, Denver, Colo.) to prevent UV-induced DNA damage that could impact subsequent manipulations, including in vitro transcription. It was found that increased concentrations of full-length transcripts and increased transfection efficiencies were achieved after Dark Reader technology was used to isolate the TGEV cDNAs.

Figure 1C:
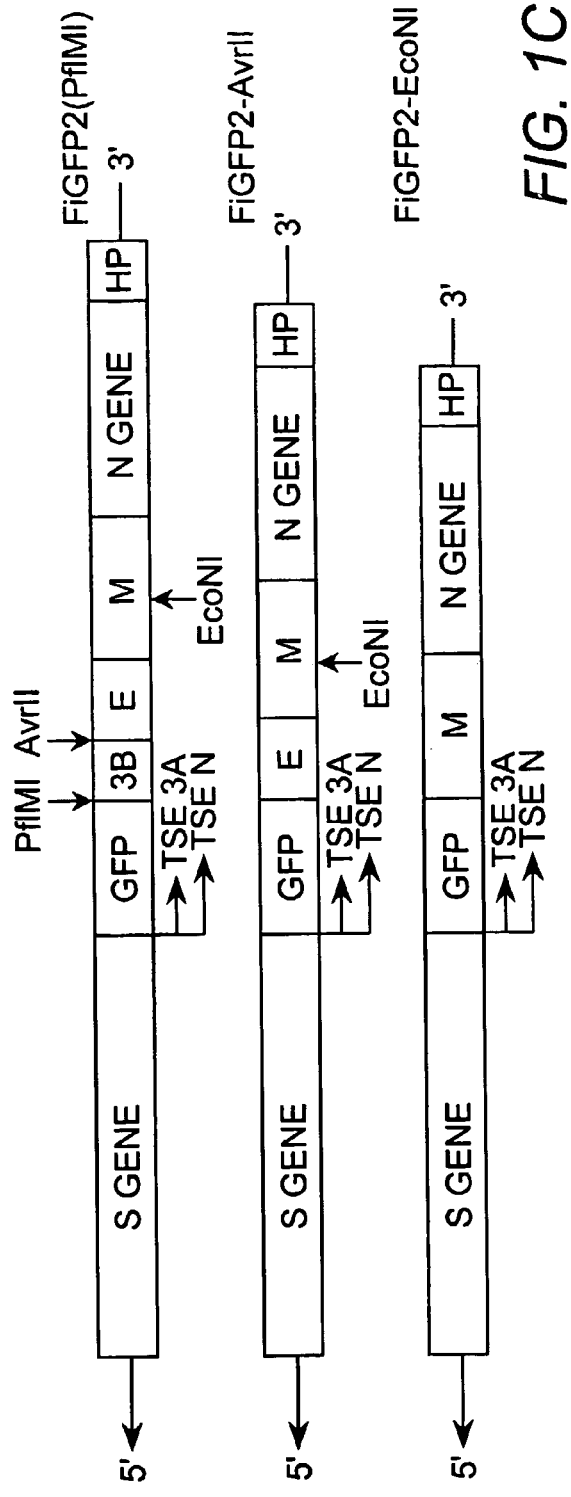
FIG. 1C shows the organization of TGEV recombinant fragments encoding GFP. FiGFP2(PflMI) was constructed by deleting ORF 3A and inserting GFP with a 5' 20-nt N gene TSE. Subsequent deletions extending from the unique PflMI to the unique AvrII and EcoNI sites generated FiGFP2-AvrII and FiGFP2-EcoNI fragments, respectively.
Figure 1D:
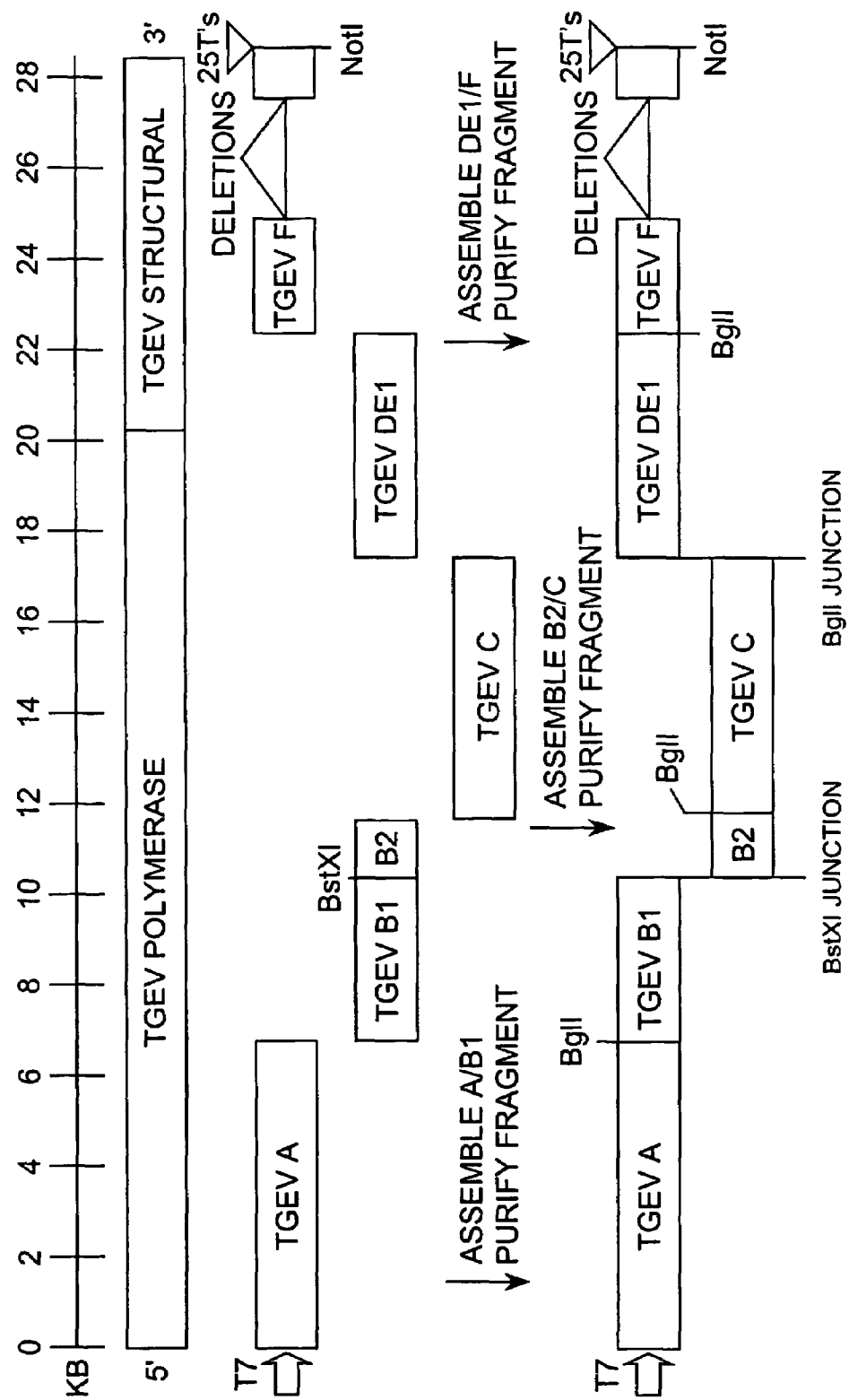
FIG. 1D depicts the strategy for assembling recombinant TGEV and replicon cDNAs. The six cDNA subclones (TGEV A, B1, B2, C, DE1, and F deletion fragments) spanning the genome are flanked by unique interconnecting BglI and BstXI sites, allowing for directional assembly into a full-length replicon cDNA by in vitro ligation. TGEV A contained a unique T7 start site at the 5' end and the deletion fragments (FiGFP2-AvrII and FiGFP2-EcoNI) contain GFP and a 25-nt T tail, allowing for the synthesis of capped T7, polyadenylated transcripts in vitro.
Figure 2:
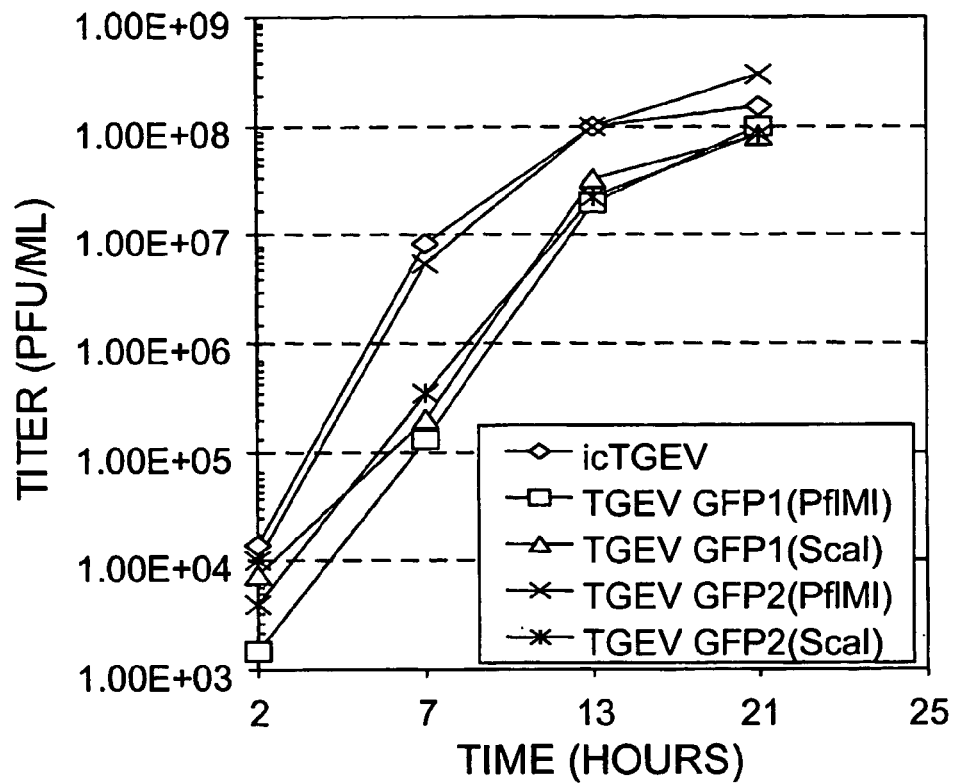
FIG. 2 depicts the growth kinetics of recombinant TGEV. ST cells were infected with TGEV GFP recombinant viruses or icTGEV 1000.

Six subgenomic cDNA clones (A to F) spanning the entire TGEV genome were isolated using standard molecular techniques as previously described (Yount, et al. (2000) *J. Virol.* 74:10600-10611). The 3' end of the TGEV genome, carrying the S, ORF 3A, ORF 3B, E, M, N, and ORF S genes, is contained within the 5.1-kb TGEV F subclone. To generate TGEV cDNA constructs containing a reporter gene, nucleotides 24828 to 25073 (GenBank accession no. AJ271965), corresponding to ORF 3A, were removed and replaced with the ClaI and PflMI restriction sites using conventional recombinant DNA techniques such that the adjacent ORFs (S and 3B) were not disrupted (Sambrook, et al. (1989) Molecular Cloning: a Laboratory Manual, 2nd ed. Cold Spring Harbor Laboratory Press, Cold Spring Harbor, N.Y.). The ClaI site was inserted 25 nt downstream of the 3A TSE, while the PflMI and ScaI sites are located just upstream of the ORF 3B TSE or downstream of the ORF 3B ATG start codon, respectively (FIG. 1A). To potentially enhance GFP expression, the mammalian codon-optimized version of the GFP gene was isolated from the noncytopathic *Sindbis* virus vector pSINrep19/GFP (kindly provided by Charlie Rice, Columbia University) and was inserted with or without a 5' 20-nt N gene TSE (TGGTATAACTAAACTTCTAA; SEQ ID NO:17) into the TGEV genome (FIG. 1B). The TGEV ORF 3A (ClaI/PflMI digestion), and in some instances a portion of ORF 3B (ClaI/ScaI digestion), were removed and replaced with GFP in several orientations (FIG. 1A) using standard recombinant DNA techniques (Sambrook, et al. (1989) Molecular Cloning: a Laboratory Manual, 2nd ed. Cold Spring Harbor Laboratory Press, Cold Spring Harbor, N.Y.). In TGEV iGFP2(ScaI), an ATG start codon was inserted between the ORF 3A and N TSEs to ablate expression from ORF 3A TSE-derived transcripts (FIG. 1B). Clones were identified by DNA sequencing using an ABI model 377 automated sequencer and constructs TGEV pFiGFP2(PflMI) and TGEV iGFP2(ScaI) were subsequently used in the assembly of recombinant TGEV viral cDNA and as the backbone for the construction of structural gene deletions (FIG. 1D).

EXAMPLE 3

Assembly of Full-Length TGEV cDNAs

The six cDNA subclones spanning the entire TGEV genome, including the FiGFP2(PflMI) and FiGFP2(PflMI) deletion subclones, were used to assemble TGEV viral and replicon constructs, respectively, as previously described (FIG. 1D) (Yount, et al. (2000) *J. Virol.* 74:10600-10611; Curtis, et al. (2002) *J. Virol.* 76:1422-1434). The TGEV A fragment contains a T7 promoter while the TGEV FiGFP2 (PflMI), FiGFP2-AvrII, and FiGFP2-EcoNI fragments terminate in a 25-nt poly(T) tract and a unique NotI site at the 3' end, allowing for in vitro T7 transcription of capped, polyadenylated transcripts (FIG. 1C). To assemble full-length TGEV recombinant virus and subgenomic replicon cDNAs, plasmids were digested with BglI and BstXI or NotI, and the appropriately-sized inserts were isolated from agarose gels. The TGEV A-B1, B2-C, and DE-1-FiGFP2 fragments were ligated overnight at 4° C. in the presence of T4 DNA ligase, according to the manufacturer's directions. Systematically, assembled products were isolated and extracted from agarose gels, and the TGEV A-B1, B2-C, and DE-1-FiGFP2 fragments were religated overnight. The final ligation products were purified by phenol-chloroform-isoamyl alcohol and chloroform extraction, precipitated under isopropanol, and washed with 70 and 90% ethanol. Purified TGEV full-length viral and replicon cDNA constructs, designated TGEV-GFP2(PflMI), TGEV-Rep(AvrII), and TGEV-Rep(EcoNI), were subsequently used for T7 in vitro transcription. The resulting replicon RNAs from Rep (AvrII) and TGEV-Rep(EcoNI) T7 in vitro transcription were ~29.1 kb and 28.4 kb, respectively.

EXAMPLE 4

TGEV in vitro Transcription and Transfection

Figure 3A:
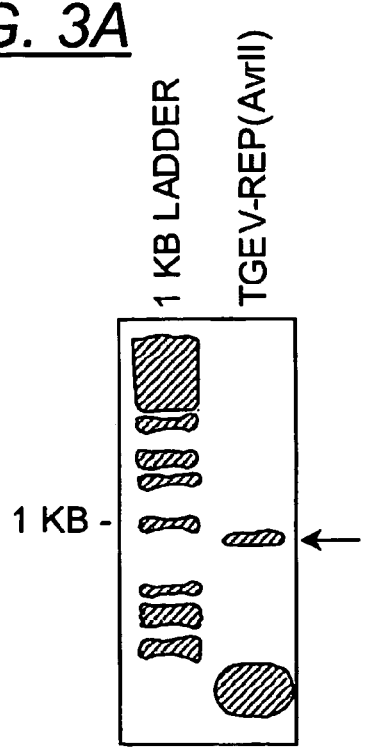
FIG. 3A shows RT-PCR products of leader-containing GFP transcripts from cells transfected with TGEV-Rep (AvrII). Arrow indicates leader-containing GFP amplicon.
Figure 3B:
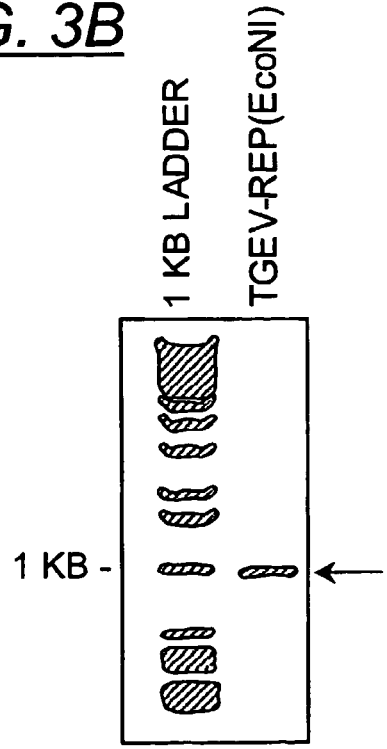
FIG. 3B shows RT-PCR products of GFP derived from cells transfected with TGEV-Rep(EcoNI). Arrow indicates leader-containing GFP amplicon.

The TGEV A fragment contains a T7 promoter while the TGEV FiGFP2(PflMI) fragment has a poly(T) tract at its very 3' end, allowing for in vitro T7 transcription of capped, polyadenylated mRNAs. Capped, runoff T7 transcripts were synthesized in vitro from assembled TGEV and replicon cDNAs using the MMESSAGE MMACHINE™ kit as described by the manufacturer (Ambion, Austin, Tex.), with certain modifications. TGEV RNA transcription reaction mixtures (50-μl volume) were prepared containing 7.5 μl of a 30 mM GTP stock and incubated at 37° C. for 2 h. Similar reactions were performed using 1 μl of PCR amplicons carrying the TGEV N gene sequence and 1 μg of pVR21-E1, each containing a 2:1 ratio of cap analog to GTP. A portion of the RNA transcripts (5 μl of the 50-μl reaction volume) were treated with DNase I, denatured, and separated in 0.5% agarose gels in Tris-acetate-EDTA buffer containing 0.1% sodium dodecyl sulfate. The remaining RNA transcripts were mixed with transcripts encoding TGEV N and directly electroporated into BHK cells. As a control, separate transcription reaction mixtures were treated with RNase A for 15 min at room temperature prior to transfection. Using transcripts driven from various pSin replicons as a control, it was predicted that the transcripts generated from the replicon cDNAs were likely of the appropriate lengths.

BHK cells were grown to subconfluence (~70%), trypsinized, washed twice with PBS, and resuspended in PBS at a concentration of $10^7$ cells/ml. RNA transcripts were added to 800 μl of the cell suspension ($8 \times 10^6$ cells) in an electroporation cuvette, and three electrical pulses of 850 V at 25 μF were given with a Bio-Rad Gene Pulser II electroporator. N gene transcripts (lacking the TGEV leader sequence) were included in all electroporations, as these transcripts may enhance the recovery of infectious TGEV virions derived from the full-length cDNA construct, TGEV 1000 (Yount, et al. (2000) *J. Virol.* 74:10600-10611). The BHK cells were either seeded alone or, in some instances, mixed with $10^6$ ST cells in a 75-$cm^2$ flask and incubated at 37° C. in 5% $CO_2$. Aliquots of cell culture supernatants were harvested ~36 h post-electroporation, and fresh cultures of ST cells were infected for 1 h at room temperature and subsequently incubated at 37° C. in complete medium.

Recombinant TGEV strains all displayed growth kinetics similar to those of wild-type TGEV generated from the TGEV 1000 infectious construct, with all viruses growing to ~$10^8$ PFU/ml in ~20 h (FIG. 2). Clearly, TGEV ORF 3A and 3B are not required for TGEV replication in vitro.

EXAMPLE 5

Analysis of GFP Expression and RT-PCR to Detect Leader-Containing Sub-Genomic Transcripts At ~14-18 h post-electroporation, transfected cultures were analyzed for GFP expression by fluorescent microscopy using an Olympus model inverted microscope. High levels of GFP expression from TGEV-GFP2, but not from the wild-type virus, were evident by fluorescence microscopy. Recombinant TGEV-GFP2 was stable for at least 10 high-titer passages in ST cells, as demonstrated by high levels of GFP expression.

GFP expression was observed in 1% of the cells transfected with TGEV-Rep(AvrII) and TGEV-Rep(EcoNI) RNAs, demonstrating that TGEV ORF 3A, ORF 3B, E, and M were not required for subgenomic mRNA synthesis and GFP expression. Transcripts of TGEV-Rep(AvrII) and TGEV-Rep(EcoNI) treated with RNase A prior to transfection did not result in observable GFP expression. Leader-containing subgenomic transcripts should be present that encode GFP and contain the appropriate deletions that were introduced into the replicon cDNAs. Consequently, total intracellular RNA was harvested from transfected cell cultures (pass 0) with Trizol reagent (Gibco BRL, Carlsbad, Calif.) and from cultures inoculated with pass 0 supernatants (pass 1) at ~36 h post-infection and was used as a template for reverse transcription-PCR (RT-PCR) using primer sets to detect leader-containing transcripts encoding GFP.

RT reactions were performed using SUPERSCRIPT™ II reverse transcriptase for 1 h at 42° C. (250 mM Tris-HCl [pH 8.3], 375 mM KCl, 15 mM $MgCl_2$, 0.1 M dithiothreitol), as described by the manufacturer (Gibco BRL), prior to PCR amplification using Taq polymerase (Expand Long kit; Roche Biochemical, Indianapolis, Ind.). To detect leader-containing GFP transcripts in TGEV-GFP2-infected cells, the 5' leader-specific primer (nt 1 to 25) TGEV-L (5'-CAC TAT AGA CTT TTA AAG TAA AGT GAG TGT AGC-3'; SEQ ID NO:18) was used with the 3' primer F:5010(−)(5'-ATT AAG ATG CCG ACA CAC GTC-3'; SEQ ID NO:19), located within ORF 3B at position 24828. To detect leader-containing GFP transcripts derived from replicon RNAs, two different primer sets were utilized. The 5' leader-specific primer, TGEV-L, was used with the 3' primer (−)E5546 (5'-GTT AAT GAC CAT TCC ATT GTC-3'; SEQ ID NO:20), located just downstream of the AvrII site within TGEV E at nucleotide position 25866, to amplify across the PflMI-AvrII deletion. To amplify across the PlfMI-EcoNI deletion, the same 5' leader-specific primer (TGEV-L) was used with the 3' primer M6400(−)(5'-CAA GTG TGT AGA CAA TAG TCC-3'; SEQ ID NO:21), located just downstream of the EcoNI site within TGEV M at nucleotide position 26624. Following 30 cycles of amplification (94° C. for 25 s, 60° C. for 25 s, 68° C. for 90 s), PCR products were separated on agarose gels and visualized by using Dark Reader technology (Clare Chemical Research). All images were digitalized and assembled by using Adobe Photoshop® 5.5 (Adobe Systems, Inc., San Jose, Calif.).

Appropriately sized amplicons of ~850 bp were generated from the TGEV-Rep(AvrII)- and TGEV-Rep(EcoNI)-transfected cells (FIG. 3A and FIG. 3B, respectively), corresponding to leader-containing GFP transcripts. Subsequently, the TGEV-Rep(EcoNI) amplicon was isolated and subcloned directly into TOPO® XL TA cloning vectors (INVITROGEN™, Carlsbad, Calif.) as described by the manufacturer. Colonies were isolated on Luria-Bertani plates containing kanamycin (50 μg/ml), and plasmid DNAs were sequenced using an ABI model 377 automated sequencer.

Sequence information confirmed the synthesis of leader-containing GFP transcripts with the PflMI-EcoNI deletion that originated from the ORF 3A TSE. Identical results were seen following TGEV-GFP2 infection, indicating that the 20-nt N gene TSE was silent in this configuration and that the natural ORF 3A TSE was preferentially used in subgenomic mRNA synthesis. Moreover, TGEV iGFP2(ScaI), which has an ATG start codon flanked by the 3A and N gene TSE sites, expressed very low levels of GFP (FIG. 3C). Sequence analysis from over 30 independent clones has confirmed that the GFP subgenomic mRNAs originate from 3A, but not N TSE. This was surprising as: 1) The N gene TSE is the strongest initiator of subgenomic RNAs (Jeong, et al. (1996) *Virology* 217:311-322; Makino, et al. (1991) *J. Virol.* 65:6031-6041; Schaad and Baric (1994) *J. Virol.* 68:8169-8197), and 2) the transcription attenuation model predicts that downstream TSE sites repress expression from upstream sites (Krishnan et al. (1996) *Virology* 218:400-405; Sawicki and Sawicki (1990) *J. Virol.* 64:1050-1056). The most likely interpretation of these data is that the N TSE site and its surrounding flanking sequence regulates transcription attenuation of subgenomic RNAs. In the absence of the appropriate flanking sequence, the N TSE is inactive.

In contrast, wild-type TGEV-infected cells yielded multiple amplicons corresponding to leader-containing transcripts carrying TGEV ORF 3A, ORF 3B, E, and M. These transcripts were not detected in TGEV-Rep(AvrII)- and TGEV-Rep(EcoNI)-electroporated cells, respectively, as these genes were completely or partially deleted in the TGEV-Rep constructs (FIG. 1C). Taken together, these data demonstrate the synthesis of subgenomic mRNA and heterologous gene expression from the TGEV-Rep(AvrII) and TGEV-Rep(EcoNI) subgenomic replicon RNAs.

EXAMPLE 6

Analysis of PRRSV GP5 Heterologous Expression

Figure 4A:
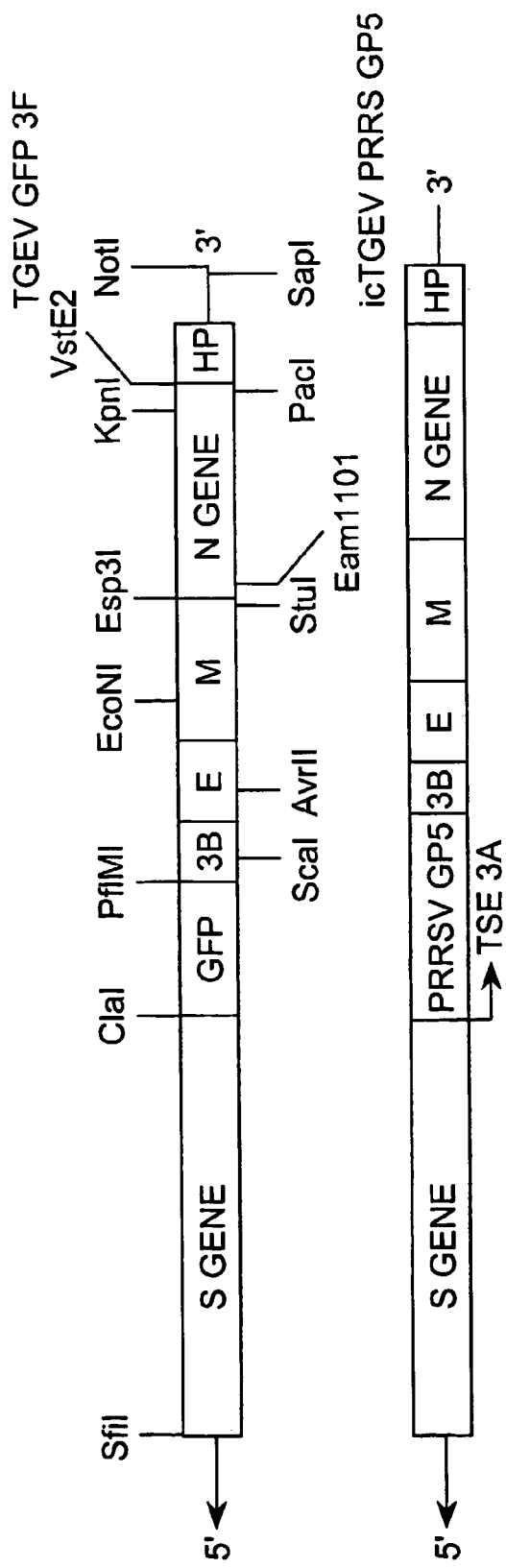
FIG. 4A depicts the structure of constructs expressing recombinant PRRS GP5.
Figure 4B:
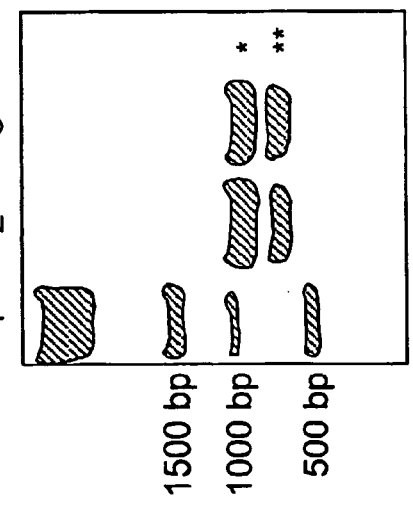
FIG. 4B shows the icTGEV PRRS GP5 leader-containing transcripts in infected cells. A 1-kb ladder is shown in lane 1.

Previous studies have demonstrated that the PRRSV M protein accumulates in the ER of infected cells where it forms disulfide-linked heterodimers with GP5. Heterodimer formation may be critical in eliciting neutralizing antibody against conformational epitopes (Balasuriya, et al. (2000) *J. Virol.* 74:10623-30). Using the TGEV 3F subclone (FIG. 4A), GFP was removed by ClaI/PflMI digestion and replaced with GP5 of PRRSV to create icTGEV PRSS GP5 recombinant viruses (FIG. 4A). Recombinant viruses expressed PRRSV GP5 antigen as determined by Fluorescent Antibody analysis and by RT-PCR amplification of the gene (FIG. 4B) using primer pairs within the TGEV leader and PRRSV PG5. Leader-primed GP5 PCR amplicon should be about 750 bp (*; lanes 2 and 3), note the smaller PCR amplicon which likely represents cryptic TSE starts (**).

EXAMPLE 7

Gene Order Mutants and Transcription

Figure 5:
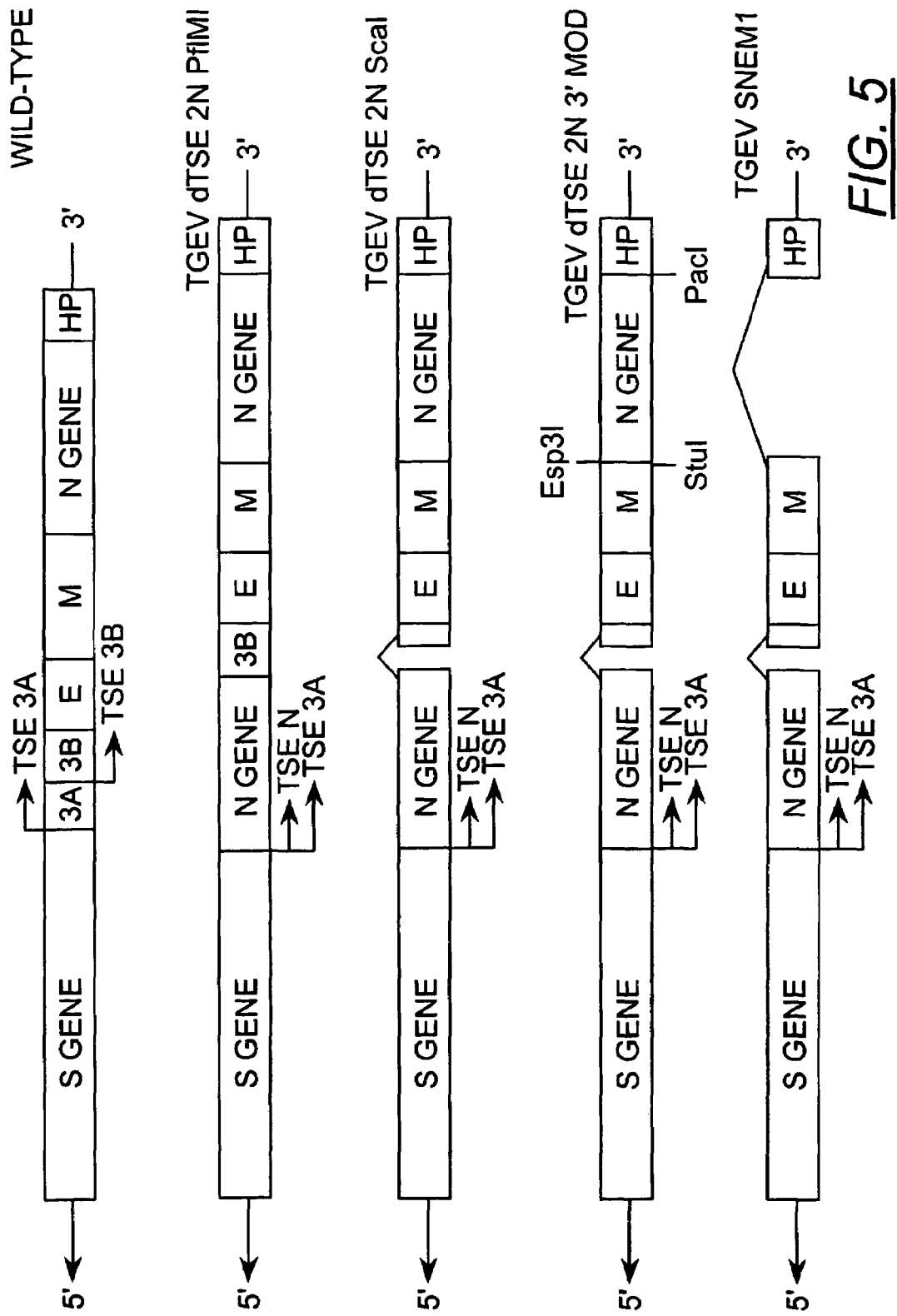
FIG. 5 depicts the structure of the TGEV N gene rearranged viruses. The TGEV N gene and TSE were inserted downstream of the 3A TSE site by removing the ORF 3A (TGEV 2N(PflMI)) or ORF 3A and a part of ORF 3B (TGEV 2N(ScaI)). The downstream N gene was flanked by restriction sites and removed to produce the SNEM rearranged viruses.
Figure 7:
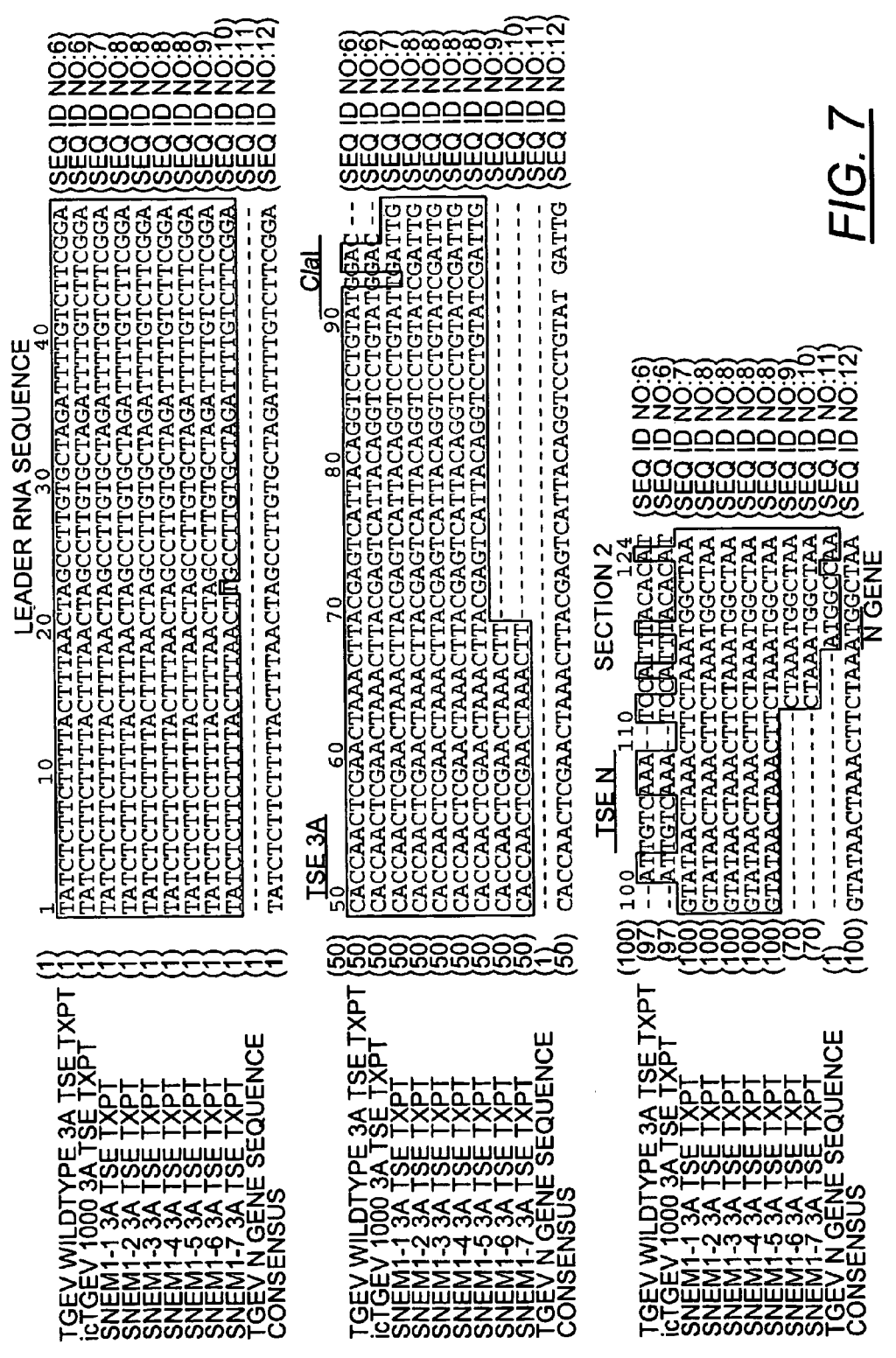

The results provided above suggest that flanking sequences enhance transcription from the N TSE element. To test this hypothesis, GFP was replaced with the TGEV N gene and N TSE site as shown in FIG. 5. TGEV recombinant viruses were isolated that contained two copies of the N gene (TGEV 2N) as well as TGEV SNEM rearranged viruses that lack the "natural N orientation, and express N from the ORF3 position (FIG. 5). TGEV 2N recombinant viruses were viable and replicated efficiently in ST cells($10^7$), demonstrating that gene duplication does not significantly interfere with TGEV replication (FIG. 6). Stability of the TGEV 2N constructs has not yet been studied (Beck and Dawson (1990) *Virology* 177:462-469). In contrast, the TGEV SNEM gene order mutant TGEV SNEMp4A, purified at passage 4 after the initial transfection, were not robust, only replicating to $\sim 9.0 \times 10^4$ PFU/ml. After 9 serial passages of the initial transfection progeny, however, TGEV SNEM1 and 4 viruses were isolated that replicated to titers of $\sim 10^6$ PFU/ml, and each retained N gene expression from the ORF3 position (FIG. 7 and FIG. 8). Sequence analysis has indicated that about 85% of the N gene leader-containing transcripts initiated from the 3A TSE site in TGEV SNEM1, TGEV SNEM4, TGEV 2N-1(PflMI) and TGEV 2N(ScaI) viruses. However, about 15% of the leader-containing transcripts initiated from the N TSE site, supporting the hypothesis that flanking sequences effect N TSE function (FIG. 7)(Alonso, et al (2002) *J. Virol.* 76:1293-308). These data demonstrate that gene order mutants of TGEV are viable, similar to results described for VSV (Ball, et al. (1999) *J. Virol.* 73:4705-4712)

To test the hypothesis that compensatory evolution was restoring SNEM virus fitness, TGEV SNEM1 and SNEM4 were serially-passaged 15 times in ST cells. Plaque purified viruses (TGEV SNEM1p15A and TGEV SNEM4p15B) replicated to high $\sim 10^7$ to $10^8$ PFU/ml, respectively within about 24 hrs postinfection (FIG. 6). Cultures of ST cells were infected and the "TGEV F fragment" of the TGEV SNEM1 and 4 and revertant viruses were cloned and sequenced (see FIG. 8). SNEM virus fitness was not recovered by recombination events that restored the natural gene order. In contrast to the parental replication impaired TGEV SNEMp4A virus, residual ORF 3B sequences were deleted in TGEV SNEM1 (nucleotides 25,287-25,832) and SNEM 4 (25,197-25,833). As the E TSE is located at position 25,813-25,819 (Almazan, et al. (2000) *Proc. Natl. Acad. Sci. USA* 97:5516-5521), it is apparently not needed for transcription of subgenomic mRNAs encoding the E protein—an essential gene for virion assembly (Fischer, et al. (1998) *J. Virol.* 72:7885-7894; Vennema, et al. (1996) *EMBO J.* 15:2020-2028). In TGEV SNEM1 viruses, a related TSE motif ACAAAAC (SEQ ID NO:13), is located at position 25,275-282 and may serve as an E TSE site. However, no obvious E TSE sites are present in the TGEV SNEM4 viruses. It is hypothesized that these deletions have enhanced TGEV SNEM1 and 4 replication by creating a new E transcriptional regulatory sequence (TRS) and thereby, altering transcription of both the TGEV N and E subgenomic RNAs. Importantly, these findings provide additional support for the hypothesis that the core TSE motif ACTAAAC (SEQ ID NO:1), is a junction site and that other flanking sequences function as regulatory sequences of transcription. The TGEV SNEM1p15A and SNEM4p15B revertants have retained the ORF 3B deletions, and also contain different sets of replacement mutations in the E and M glycoproteins. It is not clear how these changes may enhance virus replication or whether additional mutations may be encoded outside of the F fragment. For vaccine purposes, these data indicate that robust gene order rearranged *Coronaviruses* can be assembled and used as safe heterologous vaccines in swine and other vertebrates.

EXAMPLE 8

Assembly of TGEV Replicons Encoding GFP

The data presented herein demonstrate that an ORF 3A deletion is not detrimental to stable replication and passage of recombinant TGEV expressing GFP. Consequently, replicon constructs were generated by deleting the E and M structural genes from the previously constructed FiGFP2 (PflMI) F fragment (FIG. 1C).

Serial deletions within the TGEV structural gene region were generated from the unique PflMI site at the very 3' end of the GFP gene and extended for various distances toward the 3' end of the genome (FIG. 1C). In the first construct (pFiGFP2-AvrII), TGEV ORF 3B and the very 5' end of the E gene (first 10 nt), including the E gene TSE and ATG start codon, were removed by PflMI-AvrII digestion. After the digestion, the plasmid was treated with T4 DNA polymerase under conditions in which the 5'→3' exonuclease activity generated blunt ends (according to the manufacturer's directions; New England BioLabs) and religated using T4 DNA ligase. The result was an ~800-nt deletion from pFiGFP2 (PflMI).

In the second construct (pFiGFP2-EcoNI), ORF 3B, E, and the 5'-most 508 nt of the M gene, including the M gene TSE, were removed by PflMI-EcoNI digestion, treated with T4 DNA polymerase to generate blunt ends, and religated using T4 DNA ligase. The result was an ~1.5-kb deletion.

The unique AvrII site is located at nucleotide position 25866 within the E protein gene, and the unique EcoNI site is located at nucleotide position 26624 within the M protein gene (Almazan, et al. (2000) *Proc. Natl. Acad. Sci. USA* 97:5516-5521). Clones containing each of the deletions were identified by restriction digestion analysis and confirmed by DNA sequencing using an ABI model 377 automated sequencer. The new TGEV F fragments (FiGFP2-AvrII and FiGFP2-EcoNI) were subsequently utilized in the assembly of full-length TGEV replicon constructs (FIG. 1C).

EXAMPLE 9

Replication Competence of TGEV Replicon RNAs

TGEV-Rep(AvrII) lacks all of ORF 3B and a portion of the E gene and therefore should not produce infectious virions. Successful assembly of infectious TGEV from this replicon should be prevented on at least two levels. First, the E gene TSE and flanking sequences have been deleted in this replicon, which should preclude the synthesis of E gene subgenomic mRNA transcripts. Secondly, the E gene start codon has been deleted, and the next possible ATG start codon is out of the E gene reading frame at nucleotide position 25888 and would potentially encode an irrelevant 14-amino-acid protein. However, one possible in-frame E gene start codon is located 33 bp downstream of the PflMI-AvrII deletion, at nucleotide position 25899, and expression from this site would result in a truncated E protein, with about a 17% (14 of 83 amino acids) deletion from the N-terminus, including residues within a putative membrane anchor. Although unlikely, the expression of a biologically active, truncated E protein may result via read-through from other TGEV mRNAs or from cryptic TSE sites that drive expression of a subgenomic mRNA encoding the E protein, allowing for the assembly of infectious virions. This may be unlikely, as cryptic subgenomic leader-containing E transcripts were not detected by RT-PCR that would encode this E protein truncation. To address whether small amounts of truncated E are produced which function in virus assembly and release, aliquots of cell culture supernatants were harvested ~36 h post-electroporation and passed onto fresh cultures of ST cells (pass 1). By RT-PCR, there was no evidence of virus replication. In addition, virus-induced cytopathology and GFP expression were not apparent in these cultures.

EXAMPLE 10

Recombinant VEE Replicon Construct

Figures 10, 11A, 11B, 12:
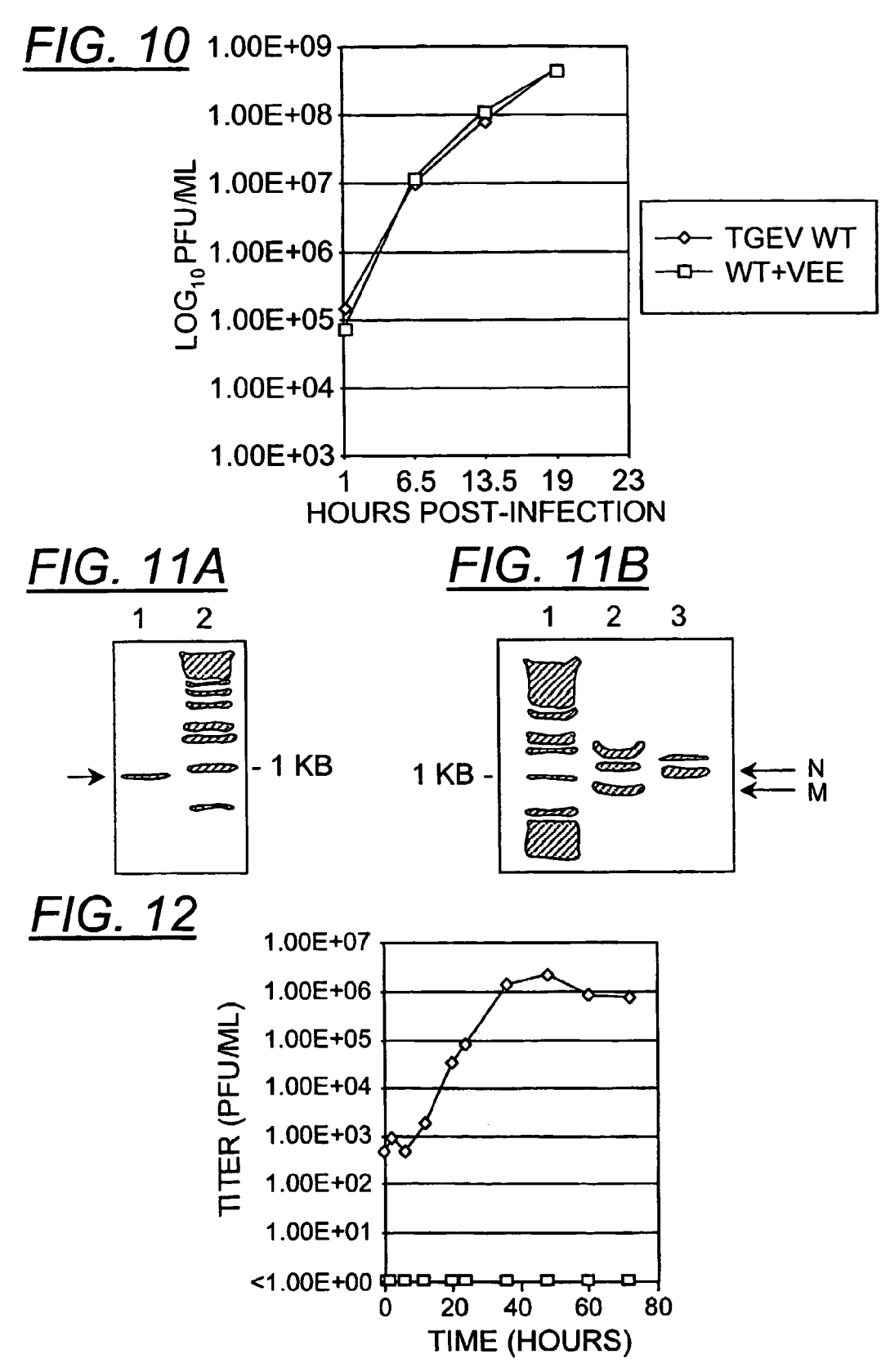

Previous data indicate that the PflMI-AvrII deletion prevented E protein function and the assembly of infectious virus. Consequently, E protein provided in trans should complement the E gene deletion and result in infectious TGEV VRPs. The VEE replicon system has been used previously for the high-level expression of a number of heterologous genes (Balasuriya, et al. (2000) *J. Virol.* 74:10623-10630; Caley, et al. (1997) *J. Virol.* 71:3031-3038; Hevey, et al. (1998) *Virology* 251:28-37; Pushko, et al. (2000) *Vaccine* 19:142-153; Pushko, et al. (1997) *Virology* 239:389-401; Schultz-Cherry, et al. (2000) *Virology* 278:55-59) and was used as an efficient means for expressing the TGEV E protein in trans. It was hypothesized that VEE VRPs expressing TGEV E would supply sufficient concentrations of E protein in trans to allow for efficient assembly and release of packaged TGEV-Rep(AvrII) VRPs (FIG. 9). To determine the effect of VEE VRPs on TGEV replication, cultures of ST cells were either infected with wild-type TGEV alone or coinfected with VEE VRPs containing a G1 VEE-NCFL capsid gene (Harrington, et al. (2002) *J. Virol.* 76:730-742) and wild-type TGEV. Progeny TGEV virions were harvested at different times post-infection and quantified by plaque assay in ST cells (FIG. 10). Clearly, the TGEV growth rate was not adversely affected by co-infection with VEE VRPs. Similar results have been shown with another alpha-virus, *Sindbis* virus, and the murine *coronavirus* mouse hepatitis virus (MHV) (Baric, et al. (1999) *J. Virol.* 73:638-649).

The TGEV E gene was inserted into the VEE replicon vector pVR21, kindly provided by Nancy Davis and Robert Johnston (Balasuriya, et al. (2000) *J. Virol.* 74:10623-10630). Using overlapping extension PCR, the TGEV E gene was inserted just downstream of the subgenomic 26S promoter within the multiple cloning site of pVR21. Using the Expand Long Template PCR system (Roche Molecular Biochemicals), the TGEV (Purdue strain) E gene was amplified from the TGEV F fragment by 30 cycles of PCR (94° C. for 25 s, 60° C. for 25 s, 72° C. for 1 min) by u the TGEV E(V+) 5' primer (5'-AGT CTA GTC CGC CAA GAT GAC GTT TCC TAG GGC ATT G-3'; SEQ ID NO:22) and the AscI site-containing TGEV E(V−) 3' primer (5'-GGC GCG CCT CAA GCA AGG AGT GCT CCA TC-3'; SEQ ID NO:23). In addition, a segment of the pVR21 vector containing a unique SwaI site followed by the 26S subgenomic promoter was amplified by PCR by using the 6198V primer (5'-GCA AAG CTG CGC AGC TTT CC; SEQ ID NO:24) with the (−)7564V primer (5'-CAT CTT GGC GGA CTA GAC TAT GTC GTA GTC CAT TCA GGT TAG CCG; SEQ ID NO:25). Appropriately-sized amplicons were isolated on agarose gels and extracted as previously described (Yount, et al. (2000) *J. Virol.* 74:10600-10611).

The 5'-most 19 nt of primer (−)7546V were complementary to the 5'-most 19 nt of the 5' TGEV E(V) primer, allowing for the adjoining of the two amplicons by overlapping PCR. Using the Expand Long Template PCR system, reactions were performed and consisted of 30 cycles of 94° C. for 20 s, 58° C. for 30 s, and 68° C. for 2 min, with the first 5 cycles done in the absence of primers. The resulting amplicon, containing unique SwaI and AscI restriction sites at its 5' and 3' ends, respectively, was isolated and purified as previously described. Following AscI and SwaI restriction digest (unique to both the TGEV E amplicon and pVR21), the TGEV E gene was inserted into the pVR21 vector. The resulting recombinant VEE replicon vector (pVR21-E1) was cloned, and the sequence was confirmed using an ABI model 377 automated sequencer. pVR21-E1 was subsequently used for the production of VEE VRPs expressing the TGEV E protein [VEE-TGEV(E)].

A bipartite helper system consisting of two helper RNAs derived from the V3014Δ520-7505 monopartite helper was used for the construction of VEE replicon particles (Pushko, et al. (2000) *Vaccine* 19:142-153). These helper RNAs express the individual capsid and glycoprotein genes of VEE, thereby supplying the structural genes in trans.

EXAMPLE 11

Recombinant VEE VRP Production

The recombinant VEE replicon construct (pVR21-E1) was linearized at a site downstream of the VEE cDNA sequence by NotI digestion, and T7-capped runoff transcripts were generated in vitro by using the T7 mMessage mMachine™ kit as described by the manufacturer (Ambion). Recombinant VEE replicon and helper RNAs were co-electroporated into BHK cells and incubated at 37° C. in 5% $CO_2$ for ~24 to 27 h. Cell culture supernatants were harvested and clarified by centrifugation at 12,000×g for 15 min. Recombinant VEE VRPs (VEE-TGEV[E]) were partially purified, concentrated, and resuspended in PBS as previously described (Davis, et al. (2000) *J. Virol.* 74:371-378). Although we were unable to quantitatively identify the presence of VEE-TGEV(E) VRPs due to our lack of anti-E antibody, a qualitative analysis was performed. BHK cells were infected with purified VEE-TGEV(E) VRPs for 1 h at room temperature. VRP titers were high as cytopathic effects were evident in 100% of the transfected cultures, suggesting titers of >$10^8$ VRP/ml, and transcripts encoding TGEV E were present in infected cells as detected by RT-PCR amplification of leader-containing transcripts.

EXAMPLE 12

Packaging of TGEV Replicon RNA

Two methods were used to supply TGEV E in trans, allowing for the packaging of TGEV-Rep(AvrII) replicon RNA. In the first method, TGEV-Rep(AvrII) replicon RNA and the helper RNA derived from pVR21-E1 were co-electroporated into BHK cells. In the second method, BHK cells were first electroporated with in vitro-transcribed TGEV-Rep(AvrII) RNA (pass 0), seeded onto 75-cm² flasks of ST cells, and at 3 h post-electroporation, subsequently infected with recombinant VEE-TGEV(E) VRPs for 1 h at room temperature. Cultures were visualized for GFP expression by fluorescent microscopy at ~18 h post-electroporation. In both methods, GFP expression was evident by fluorescent microscopy, demonstrating the subgenomic transcription and heterologous gene expression from the TGEV-Rep(AvrII) genome in the presence of VEE replicon RNAs. Conversely, passage of supernatants from cells tranfected with TGEV-Rep(AvrII) transcripts without expression of the E protein in trans did not result in detectable GFP expression.

Cell culture supernatants were harvested ~36 h post-transfection and undiluted aliquots were used to inoculate fresh cultures of ST cells cultures (75-cm² flasks) (pass 1) for 1 h at room temperature to determine if the TGEV-Rep (AvrII) replicon RNA had been packaged into TGEV VRPs. Successful packaging and passing of TGEV-Rep(AvrII) replicon RNA were determined by GFP expression, and RT-PCR analysis was performed to detect leader-containing GFP transcripts, as described above. By ~18 h post-infection, GFP expression was observed in these pass 1 cultures, confirming that replicon RNAs had been packaged into infectious TGEV VRPs. However, TGEV VRP titers were low, estimated to be $10^3$ to $10^5$ infectious units/ml by fluorescent microscopy, depending on the experiment. TGEV VRPs should express leader-containing subgenomic mRNAs encoding GFP and the various downstream ORFs, including M and N. Following TGEV VRP infection, intracellular RNA was isolated and subjected to RT-PCR by using primer pairs in the leader RNA and downstream of the GFP, M, and N genes. For this RT-PCR, primer TGEV-L 5' was used in conjunction with the 3' primers TGEV-Mg (5'-AGA AGT TTA GTT ATA CCA TAG GCC TTT ATA CCA TAT GTA ATA ATT TTT CTT GCT CAC TC-3'; SEQ ID NO:26), located at position 26870 within the M gene, and TGEV-Ng (5'-CCA CGC TTT GGT TTA GTT CGT TAC CTC ATC AAT TAT CTC-3'; SEQ ID NO:27), located at position 28038 within the N gene. Briefly, RT reactions were performed by using Superscript™ II reverse transcriptase for 1 h at 42° C. (250 mM Tris-HCl [pH 8.3], 375 mM KCl, 15 mM $MgCl_2$, 0.1 M dithiothreitol), as described by the manufacturer (Gibco BRL), prior to 30 cycles of PCR amplification using Taq polymerase (Expand Long kit; Roche Biochemical) (94° C. for 25 s, 58° C. for 25 s, 68° C. for 1 min and 40 s). PCR products were separated on agarose gels, cloned, and sequenced as previously described.

As in the previous TGEV-Rep(AvrII) experiments, a leader-containing GFP amplicon of ~850 bp was generated (FIG. 11A) and sequenced to confirm the presence of leader-containing GFP transcripts with the PflMI-AvrII deletion. Leader-containing subgenomic transcripts were also detected that contained the TGEV M and N genes, ~900 bp and ~1.2 kb, respectively (FIG. 11B), demonstrating that transcripts for at least two of the structural genes were expressed in TGEV VRP-infected cells. Larger leader-containing amplicons were also observed and likely corresponded to cryptic start sites noted within GFP as well as the larger GFP leader-containing amplicons (FIG. 11B). These data demonstrate the replication competence and heterologous gene expression from packaged TGEV-Rep(AvrII) RNAs.

EXAMPLE 13

TGEV Replicon Particles Function as Single-Hit Virus Vectors

An important aspect of viral replicon particle systems, in terms of future use as an expression vector for vaccine development, is the lack of recombinant virus production. It is possible that mutations may evolve which restore E protein expression and function or recombinant TGEVs emerge following mixed TGEV-Rep(AvrII) and VEE-TGEV (E) infection. To conclusively demonstrate the lack of recombinant virus production from the E deletion replicon RNA, 60-mm² cultures of ST cells were infected for 1 h at room temperature with TGEV VRPs obtained from previous TGEV-Rep(AvrII) packaging experiments (clarified and concentrated by high-speed centrifugation as previously described (Davis, et al. (2000) *J. Virol.* 74:371-378), overlaid with fresh media, incubated at 37° C., and subsequently examined over a 72-h time period for GFP expression by fluorescent microscopy as well as virus production by plaque assay in ST cells. Under identical conditions, supernatants obtained from cell cultures transfected with TGEV-GFP2 transcripts were passaged onto fresh ST cells and examined for virus replication by GFP expression, for cytopathic effects, and by plaque assay, as previously described.

Expansion of GFP expression was clearly observed in TGEV-GFP2-infected cells while no expansion was noted in TGEV VRP-infected cells. In fact, GFP expression in these TGEV VRP-infected cells eventually decreased after the 24-h time point and eventually disappeared. Additionally, infectious TGEV particles were not detected by plaque assay in TGEV VRP-infected cultures during this same 72-h period (FIG. 12), while infectious TGEV-GFP2 virus rapidly reached titers of $2\times10^6$ PFU/ml by 48 h post-infection under identical conditions. These data clearly demonstrate the lack of revertant wild-type and recombinant virus production from the TGEV-Rep(AvrII) VRP stocks.

The foregoing examples are illustrative of the present invention, and are not to be construed as limiting thereof. The invention is described by the following claims, with equivalents of the claims to be included therein.

What is claimed is:

1. A helper cell for producing an infectious, replication defective, coronavirus particle, wherein said cell is a coronavirus permissive cell, comprising:
   (a) a coronavirus replicon RNA comprising a coronavirus packaging signal, and a heterologous RNA sequence, wherein said replicon RNA further lacks a sequence encoding at least one coronavirus structural protein; and (b) at least one separate helper RNA encoding the at least one structural protein absent from the replicon RNA, said helper RNA lacking a coronavirus packaging signal.

wherein the combined expression of the replicon RNA and the helper RNA produces an assembled coronavirus particle which comprises said heterologous RNA sequence, is able to infect a cell, and is replication defective.

2. The helper cell according to claim 1, said replicon RNA further comprising a sequence encoding at least one of the coronavinis structural proteins.

3. The helper cell according to claim 1, wherein said helper RNA contains at least one gene encoding a structural protein selected from the group consisting of the E, M, N, and S genes.

4. The helper cell according to claim 1, wherein said helper RNA contains the E gene.

5. The helper cell according to claim 1, wherein said coronavirus is selected from the group consisting of human respiratory coronavirus, mouse hepatitis virus, porcine transmissible gastroenteritis virus, porcine respiratory *coronavirus,* canine *coronavirus,* feline enteric coronavirus, feline infectious peritonitis virus, rabbit coronavirus, murine hepatitis virus, sialodacryoadenitis virus, porcine hemagglutinating encephaloinyclitis virus, bovine *coronavirus,* avian infectious bronchitis virus, and flu-key coronavirus.

6. The helper cell according to claim 1, wherein said *coronavirus* is transmissible gastroenteritis virus.

7. The helper cell according to claim 1, wherein said replicon RNA contains at least one attenuating gene order rearrangement among the 3A, 3B, HP, S, E, M and N genes.

8. The helper cell according to claim 1, wherein said helper RNA includes a promoter.

9. The helper cell according to claim 1, wherein said replicon RNA includes a promoter.

10. The helper cell according to claim 1, wherein said heterologous RNA is selected from the group consisting of RNA encoding proteins and RNA encoding peptides.

11. The helper cell according to claim 1, further comprising a heterologous DNA encoding said helper RNA.

12. The helper cell according to claim 1, further comprising a heterologous DNA encoding said replicon RNA.

13. A method of making infectious, replication defective, coronavirus particles, comprising:

providing a helper cell according to claim 1;

producing said coronavirus particles in said helper cell; and then collecting said coronavirus particles from said helper cell.

14. The method according to claim 13, wherein said coronavinis RNA and said at least one separate helper RNA are introduced into said helper cell by electroporation.

* * * * *

UNITED STATES PATENT AND TRADEMARK OFFICE
CERTIFICATE OF CORRECTION

PATENT NO. : 7,279,327 B2 Page 1 of 1
APPLICATION NO. : 10/474962
DATED : October 9, 2007
INVENTOR(S) : Curtis et al.

It is certified that error appears in the above-identified patent and that said Letters Patent is hereby corrected as shown below:

On the title page item (56), line 23, Other Publications:

Please correct to read: --Curtis et al, "Coronavirus Derived Vectors for Genetic Analysis and Heterologous Gene Expression" *Recent Res. Devel. Virol.* 4:203-229 (2002)--

In The Claims:

Column 33, Claim 1, Line 45: Please correct "nal."
To read --nal,--

Column 33, Claim 2, Line 53: Please correct "coronavinis"
To read -- coronavirus --

Column 34, Claim 5, Line 35: Please correct "encephaloinyclitis virus"
To read -- encephalomyelitis--

Line 36: Please correct "flu-key"
To read --turkey --

Column 34, Claim 14, Line 61: Please correct "coronavinis"
To read -- coronavirus --

Signed and Sealed this

Eighteenth Day of December, 2007

JON W. DUDAS
*Director of the United States Patent and Trademark Office*

SEQUENCE LISTING

```
<160> NUMBER OF SEQ ID NOS: 27

<210> SEQ ID NO 1
<211> LENGTH: 7
<212> TYPE: DNA
<213> ORGANISM: Transmissible Gastroenteritis Virus

<400> SEQUENCE: 1 actaaac                                                              7

<210> SEQ ID NO 2
<211> LENGTH: 160
<212> TYPE: DNA
<213> ORGANISM: Transmissible Gastroenteritis Virus

<400> SEQUENCE: 2
gtccattaaa tgttaattct atcatcygct ataatagcag ttgtttctgc tagagaattt      60
tgttaaggat gatgaataaa gtctttaaga actaaactta cgagtcatta caggtcctgt     120
atcgattggt ataactaaac ttctaaatgg tgagcaaggg                           160

<210> SEQ ID NO 3
<211> LENGTH: 154
<212> TYPE: DNA
<213> ORGANISM: Transmissible Gastroenteritis Virus

<400> SEQUENCE: 3
tagccttgtg ctagattttg tcttcggaca ccaactcgaa ctaaacttac gagtcattac      60
aggtcctgta tggacattgt caaatccatt tacacatccg tagatgctgt acttgacgaa     120
cttgattgtg catactttgc tgtaactctt aaag                                 154

<210> SEQ ID NO 4
<211> LENGTH: 156
<212> TYPE: DNA
<213> ORGANISM: Transmissible Gastroenteritis Virus

<400> SEQUENCE: 4
tagccttgtg ctagattttg tcttcggaca ccaactcgaa ctaaacttac gagtcattac      60
aggtcctgta tcgatatggt ataactaaac ttctaaatgg tgagcaaggg cgaggacgtg     120
ttcaccgggg tggtgcccat cctggtcgag ctggac                               156

<210> SEQ ID NO 5
<211> LENGTH: 61
<212> TYPE: DNA
<213> ORGANISM: Artificial Sequence
<220> FEATURE:
<223> OTHER INFORMATION: Sequence of GFP.
```

-continued

```
<400> SEQUENCE: 5
atggtgagca agggcgagga gctgttcacc ggggtggtgc ccatcctggt cgagctggac    60
g                                                                    61

<210> SEQ ID NO 6
<211> LENGTH: 118
<212> TYPE: DNA
<213> ORGANISM: Transmissible Gastroenteritis Virus

<400> SEQUENCE: 6
tatctcttct tttactttaa ctagccttgt gctagatttt gtcttcggac accaactcga    60
actaaactta cgagtcatta caggtcctgt atggacattg tcaaatccat ttacacat    118

<210> SEQ ID NO 7
<211> LENGTH: 124
<212> TYPE: DNA
<213> ORGANISM: Transmissible Gastroenteritis Virus

<400> SEQUENCE: 7
tatctcttct tttactttaa ctagccttgt gctagatttt gtcttcggac accaactcga    60
actaaactta cgagtcatta caggtcctgt attgattggt ataactaaac ttctaaatgg   120
ctaa                                                                124

<210> SEQ ID NO 8
<211> LENGTH: 124
<212> TYPE: DNA
<213> ORGANISM: Transmissible Gastroenteritis Virus

<400> SEQUENCE: 8
tatctcttct tttactttaa ctagccttgt gctagatttt gtcttcggac accaactcga    60
actaaactta cgagtcatta caggtcctgt atcgattggt ataactaaac ttctaaatgg   120
ctaa                                                                124

<210> SEQ ID NO 9
<211> LENGTH: 81
<212> TYPE: DNA
<213> ORGANISM: Transmissible Gastroenteritis Virus

<400> SEQUENCE: 9
tatctcttct tttactttaa ctagccttgt gctagatttt gtcttcggac accaactcga    60
actaaacttc taaatggcta a                                              81

<210> SEQ ID NO 10
<211> LENGTH: 81
<212> TYPE: DNA
<213> ORGANISM: Transmissible Gastroenteritis Virus

<400> SEQUENCE: 10
tatctcttct tttactttaa cttgccttgt gctagatttt gtcttcggac accaactcga    60
actaaacttc taaatggcta a                                              81

<210> SEQ ID NO 11
<211> LENGTH: 8
<212> TYPE: DNA
<213> ORGANISM: Transmissible Gastroenteritis Virus
<220> FEATURE:
<221> NAME/KEY: misc_feature
<222> LOCATION: (1)..(8)
<223> OTHER INFORMATION: N Gene Sequence.
```

```
<400> SEQUENCE: 11 atggccaa                                                                8

<210> SEQ ID NO 12
<211> LENGTH: 123
<212> TYPE: DNA
<213> ORGANISM: Artificial Sequence
<220> FEATURE:
<223> OTHER INFORMATION: Consensus sequence of intergenic sequence.

<400> SEQUENCE: 12
tatctcttct tttactttaa ctagccttgt gctagatttt gtcttcggac accaactcga      60
actaaactta cgagtcatta caggtcctgt atgattggta taactaaact tctaaatggc     120
taa                                                                   123

<210> SEQ ID NO 13
<211> LENGTH: 7
<212> TYPE: DNA
<213> ORGANISM: Transmissible Gastroenteritis Virus

<400> SEQUENCE: 13 acaaaac                                                                 7

<210> SEQ ID NO 14
<211> LENGTH: 7
<212> TYPE: DNA
<213> ORGANISM: Transmissible Gastroenteritis Virus

<400> SEQUENCE: 14 actaaac                                                                 7

<210> SEQ ID NO 15
<211> LENGTH: 7
<212> TYPE: DNA
<213> ORGANISM: Transmissible Gastroenteritis Virus

<400> SEQUENCE: 15 tctaaac                                                                 7

<210> SEQ ID NO 16
<211> LENGTH: 6
<212> TYPE: DNA
<213> ORGANISM: Transmissible Gastroenteritis Virus

<400> SEQUENCE: 16 agtact                                                                  6

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 17
tggtataact aaacttctaa                                                  20

<210> SEQ ID NO 18
<211> LENGTH: 33
<212> TYPE: DNA
<213> ORGANISM: Artificial Sequence
<220> FEATURE:
```

-continued

<223> OTHER INFORMATION: Synthetic oligonucleotide primer

<400> SEQUENCE: 18
cactatagac ttttaaagta aagtgagtgt agc                          33

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 19
attaagatgc cgacacacgt c                                        21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 20
gttaatgacc attccattgt c                                        21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 21
caagtgtgta gacaatagtc c                                        21

<210> SEQ ID NO 22
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 22
agtctagtcc gccaagatga cgtttcctag ggcattg                       37

<210> SEQ ID NO 23
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 23
ggcgcgcctc aagcaaggag tgctccatc                                29

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 24
gcaaagctgc gcagctttcc                                          20

```
-continued

<210> SEQ ID NO 25
<211> LENGTH: 45
<212> TYPE: DNA
<213> ORGANISM: Artificial Sequence
<220> FEATURE:
<223> OTHER INFORMATION: Synthetic oligonucleotide primer

<400> SEQUENCE: 25
catcttggcg gactagacta tgtcgtagtc cattcaggtt agccg            45

<210> SEQ ID NO 26
<211> LENGTH: 59
<212> TYPE: DNA
<213> ORGANISM: Artificial Sequence
<220> FEATURE:
<223> OTHER INFORMATION: Synthetic oligonucleotide primer

<400> SEQUENCE: 26
agaagtttag ttataccata ggcctttata ccatatgtaa taattttct tgctcactc    59

<210> SEQ ID NO 27
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 27
ccacgctttg gtttagttcg ttacctcatc aattatctc                  39
```